United States Patent

Jikihara et al.

Patent Number: 5,442,060
Date of Patent: Aug. 15, 1995

[54] CARBOXAMIDE DERIVATIVES

[75] Inventors: Tetsuo Jikihara, Komae; Tadashi Shirasaka, Machida; Kazuo Suzuki; Hiroko Suzuki, both of Sagamihara; Masao Taniguchi, Machida; Shinya Inoue, Tokyo, all of Japan

[73] Assignee: Mitsubishi Kasei Corporation, Tokyo, Japan

[21] Appl. No.: 128,250

[22] Filed: Sep. 29, 1993

[30] Foreign Application Priority Data

Sep. 29, 1992 [JP] Japan .................. 4-260325
Sep. 30, 1992 [JP] Japan .................. 4-262476
Nov. 10, 1992 [JP] Japan .................. 4-299686

[51] Int. Cl.6 .................. C07D 265/30; C07D 295/50
[52] U.S. Cl. .................. 544/106; 544/180; 544/242; 544/358; 544/336; 546/184; 546/225; 548/400; 549/350; 549/362; 549/546; 549/570; 564/49; 564/161; 564/180; 554/35
[58] Field of Search .............. 554/35; 514/231.2, 241, 514/247, 246, 315, 316; 544/106, 180, 242, 358, 336; 548/400; 546/184, 255; 549/350, 362, 434, 570, 546; 564/49, 161, 180

[56] References Cited

FOREIGN PATENT DOCUMENTS

| | | |
|---|---|---|
| 0283742 | 9/1988 | European Pat. Off. |
| 0293880 | 12/1988 | European Pat. Off. |
| 0344425 | 12/1989 | European Pat. Off. |
| 0384320 | 8/1990 | European Pat. Off. |
| 0415123 | 3/1991 | European Pat. Off. |
| 0439059 | 7/1991 | European Pat. Off. |

*Primary Examiner*—José G. Dees
*Assistant Examiner*—Deborah D. Carr
*Attorney, Agent, or Firm*—Wenderoth, Lind & Ponack

[57] ABSTRACT

Carboxamide derivatives of the following general formula (I):

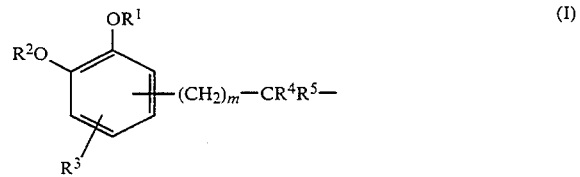

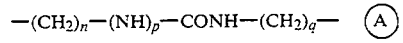

(wherein
$R^1$ and $R^2$ are $C_1$-$C_3$ alkyl group or both taken together $C_1$-$C_3$ alkylene group,
$R^3$ is hydrogen atom, dialkylamino group, etc.,
$R^4$ is hydrogen atom, $C_1$-$C_{10}$ alkyl group,
$R^5$ is $C_1$-$C_{10}$ alkyl group,
m, n, q are an integer from 0-3,
p is 0, 1,
A ring is

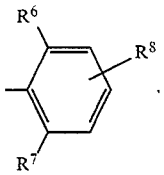

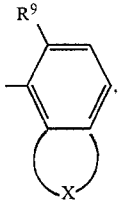

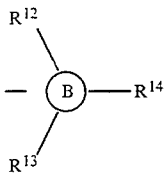

B ring is 5 or 6 membered nitrogen containing aromatic ring, are provided, which are useful as medicinals for treating hyperlipemia or atherosclerosis.

7 Claims, No Drawings

CARBOXAMIDE DERIVATIVES

The present invention relates to carboxamide derivatives having potent lipid lowering activity, and therefore, useful as medicinals for treating hyperlipemia and atherosclerosis.

Hyperlipemia due to abnormal metabolism of lipid is considered to be a cause of arteriosclerosis and also a dangerous factor of ischemic cardiac disease, cerebral infarction or the like. It has recently been shown that acylcoenzyme cholesterol acyltransferase (ACAT) plays an important role in the lipid metabolism, especially cholesterol metabolism, and it is expected that the compound having an action of inhibiting the enzyme ACAT would inhibit the absorption of cholesterol in intestines, lower the serum cholesterol, and inhibit the deposition of cholesterol on the arterial wall.

Therefore, compounds inhibiting ACAT are useful as medicinals for treating hyperlipemida and atherosclerosis.

Amide derivatives showing such ACAT inhibition are disclosed in Japanese Patent Publication (Kokoku) No. 54718/1988, Japanese Patent Kokai No. 253060/1988, Japanese Patent Kokai No. 316761/1988, Japanese Patent Kokai No. 93569/1989, Japanese Patent Kokai No. 6455/1990, Japanese Patent Kokai No. 6456/1990, Japanese Patent kokai No. 6457/1990, Japanese Patent Kokai No. 258756/1990, Japanese Patent Kokai No. 275848/1990, Japanese Patent Kokai No. 178954/1991, etc.

As the result of investigations seeking compounds showing more potent ACAT inhibition than those reported in the above publications, the present inventors have found novel and effective amide derivatives. The present invention has been established based on the finding.

Thus, the present invention relates to carboxamide derivatives represented by the following general formula (I):

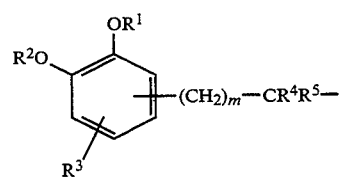  (I)

$$-(CH_2)_n-(NH)_p-CONH-(CH_2)_q- \quad \text{(A)}$$

(wherein, m, n and q each independently represent an integer from 0 to 3, p represents 0 or 1, $R^1$ and $R^2$ each independently represent $C_1$-$C_3$ alkyl group, or $R^1$ and $R^2$, taken together, may form $C_1$-$C_3$ alkylene group, $R^3$ represents hydrogen atom, amino group, $C_1$-$C_3$ alkylamino group, $C_2$-$C_6$ dialkylamino group, $C_1$-$C_3$ alkyl group, $C_2$-$C_7$ acyl group, pyrrolidino group, piperidino group, morpholino group, nitro group, hydroxy group, $C_2$-$C_7$ acyloxy group, $C_1$-$C_3$ alkoxy group or halogen atom, $R^4$ represents hydrogen atom or $C_1$-$C_{10}$ alkyl group, $R^5$ represents $C_1$-$C_{10}$ alkyl group, or $R^4$ and $R^5$ taken together may form $C_2$-$C_7$ alkylene group, A ring represents;

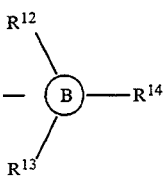

wherein $R^6$ and $R^7$ each independently represent $C_1$-$C_5$ alkyl group, $C_1$-$C_5$ alkoxy group, or halogen atom, $R^8$ represents hydrogen atom, amino group, $C_1$-$C_3$ alkylamino group, $C_2$-$C_6$ dialkylamino group, $C_1$-$C_5$ alkyl group, $C_1$-$C_5$ alkoxy group, pyrrolidino group, piperidino group, morpholino group or halogen atom; or A ring represents;

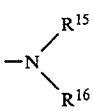

wherein $R^9$ represents hydrogen atom, $C_1$-$C_5$ alkyl group or $C_1$-$C_5$ alkoxy group and X represents;

$$-(O)_r-(CH_2)_x-CR^{10}R^{11}-(CH_2)_y-(O)_z-$$

in which $R^{10}$ and $R^{11}$ each independently represent hydrogen atom or $C_1$-$C_5$ alkyl group, r and z each independently represent 0 or 1, and x and y each independently represent an integer from 0 to 5 under the condition that $0 \leq x+y \leq 5$; or A ring represents;

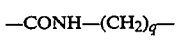

wherein B ring represents 5 or 6-membered nitrogen-containing aromatic group, $R^{12}$ and $R^{13}$ each independently represent $C_1$-$C_5$ alkyl group, optionally substituted phenyl group or piperazino group, pyridyl group, $C_1$-$C_5$ alkoxy group, a group:

$$-N\begin{matrix}R^{15}\\R^{16}\end{matrix}$$

(in which $R^{15}$ and $R^{16}$ each independently represent hydrogen atom or $C_1$-$C_5$ alkyl group, or $R^{15}$ and $R^{16}$, taken together, may form $C_3$-$C_6$ alkylene group), morpholino group, carboxy group or $C_2$-$C_4$ alkoxycarbonyl group, $R^{14}$ represents hydrogen atom or $C_1$-$C_5$ alkyl group, with the proviso that $R^{12}$ and $R^{13}$ are attached to the two atoms adjacent to the atom on the B ring which is bound to the moiety:

$$-CONH-(CH_2)_q-$$

(in which q has the same significance as defined above), with the proviso that when A ring is;

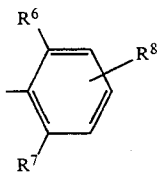

in which $R^6$, $R^7$ and $R^8$ and have the same significance as defined above, then p represents 0) or pharmaceutically acceptable salts thereof.

The present invention will be explained below in detail.

The present invention is directed to carboxamide derivatives of the following general formula (I):

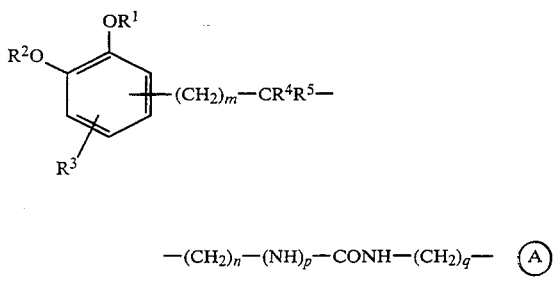

wherein, m, n and q each represent an integer from 0 to 3, p represents 0 or 1, $R^1$ and $R^2$ each independently represent $C_1$–$C_3$ alkyl group (methyl group, propyl group, etc.) or $R^1$ and $R^2$, taken together, may form $C_1$–$C_3$ alkylene group (methylene group, propylene group, etc.), $R^3$ represents hydrogen atom, amino group, $C_1$–$C_3$ alkylamino group (methylamino group, propylamino group, etc.), $C_2$–$C_6$ dialkylamino group (dimethylamino group, dipropylamino group, etc.), $C_1$–$C_3$ alkyl group (methyl group, propyl group, etc.), $C_2$–$C_7$ acyl group (acetyl group, propionyl group, benzoyl group, etc.), pyrrolidino group, piperidino group, morpholino group, nitro group, hydroxy group, $C_2$–$C_7$ acyloxy group (acetyloxy group, propionyloxy group, benzoyloxy group, etc.), $C_1$–$C_3$ alkoxy group (methoxy group, propoxy group, etc.) or halogen atom (fluorine atom, chlorine atom, bromine atom, iodine atom, etc.), $R^4$ represents hydrogen atom or $C_1$–$C_{10}$ alkyl group (methyl group, butyl group, heptyl group, decyl group, etc.), $R^5$ represents $C_1$–$C_{10}$ alkyl group (methyl group, butyl group, heptyl group, decyl group, etc.), or $R^4$ and $R^5$, taken together, may form $C_2$–$C_7$ alkylene group (e.g. ethylene group, tetramethylene group, heptamethylene group, etc.), A ring represents;

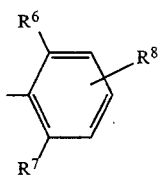

in which $R_6$ and $R_7$ each independently represent $C_1$–$C_5$ alkyl group (methyl group, propyl group, pentyl group, etc.), $C_1$–$C_5$ alkoxy group (methoxy group, propoxy group, pentyloxy group,etc.) or halogen atom (fluorine atom, chlorine atom, bromine atom, iodine atom,etc.) and $R^8$ represents amino group, $C_1$–$C_3$ alkylamino group (methylamino group, propylamino group, etc.), $C_2$–$C_6$ dialkylamino group (dimethylamino group, dipropylamino group, etc.), hydrogen, $C_1$–$C_5$ alkyl group (methyl group, propyl group, pentyl group, etc.), $C_1$–$C_5$ alkoxy group (methoxy group, propoxy group, pentyloxy group, etc.), pyrrolidino group, piperidino group, morpholino group or halogen atom (fluorine atom, chlorine atom, bromine atom, iodine atom, etc.), or A ring represents;

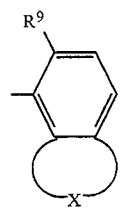

in which $R^9$ represents hydrogen atom, $C_1$–$C_5$ alkyl group (methyl group, propyl group, pentyl group, etc.) or $C_1$–$C_5$ alkoxy group (methoxy group, propoxy group, pentyloxy group, etc.), X represents;

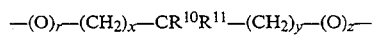

in which $R^{10}$ and $R^{11}$ each independently represent hydrogen atom or $C_1$–$C_5$ alkyl group (methyl group, propyl group, pentyl group, etc.), r and z each independently represent 0 or 1, and x and y each independently represent an integer from 0 to 5 with the proviso that $0 \leq x+y \leq 5$, or A ring represents;

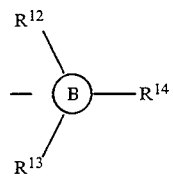

in which B ring represents 5 or 6-membered nitrogen-containing aromatic group (pyrrole ring, pyrazole ring, imidazole ring, 1, 2, 3-triazole ring, 1, 2, 4-triazole ring, isoxazole ring; pyridine ring, pyridazine ring, pyrimidine ring, etc.), $R^{12}$ and $R^{13}$ each independently represent $C_1$–$C_5$ alkyl group (methyl group, propyl group, pentyl group, etc.), phenyl group optionally substituted by a substituent such as $C_1$–$C_5$ alkyl group (methyl group, propyl group, pentyl group, etc.) or $C_1$–$C_5$ alkoxy group (methoxy group, propoxy group, pentyloxy group, etc.), piperazino group, pyridyl group, $C_1$–$C_5$ alkoxy group (methoxy, propoxy, pentyloxy, etc.), a group:

in which $R^{15}$ and $R^{16}$ each independently represent hydrogen atom or $C_1$–$C_5$ alkyl group (methyl group, propyl group, pentyl group, etc.) or $R^{15}$ and $R^{16}$, taken together, may form $C_3$–$C_6$ alkylene group (trimethylene group, hexamethylene group, etc.), morpholino group, carboxy group or $C_2$-$C_4$ alkoxycarbonyl group (methoxycarbonyl group, propoxycarbonyl group, etc.), and $R^{14}$ represents hydrogen atom or $C_1$-$C_5$ alkyl group (methyl group, propyl group, pentyl group, etc.) with the proviso that $R^{12}$ and $R^{13}$ are attached to the two atoms adjacent to the atom on the B ring which is bound to the moiety:

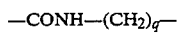
—CONH—$(CH_2)_q$— in which q has the same significance as defined above, with the proviso that when A ring is;

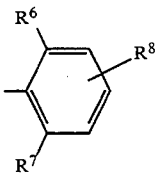

in which $R^6$, $R^7$ and $R^8$ have the same significance as defined above, then p represents 0, or pharmaceutically acceptable salts thereof.

Of the compounds of the present invention, preferred are the compounds of the general formula (I) above wherein m, p and q each independently represent 0 or 1, n represents 0, 1 or 2, $R^3$ represents hydrogen atom, $C_2$-$C_6$ dialkylamino group or $C_2$-$C_4$ acyl group, $R^4$ represents hydrogen atom, $R^5$ represents $C_1$-$C_8$ alkyl group, A ring represents;

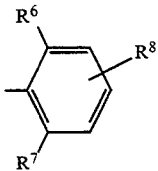

in which $R^6$ and $R^7$ each independently represent $C_1$-$C_5$ alkyl group, $C_1$-$C_3$ alkoxy group or halogen atom, $R^8$ represents hydrogen atom, $C_2$-$C_6$ dialkylamino group, $C_1$-$C_3$ alkoxy group or halogen atom, a group:

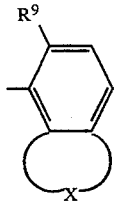

in which $R^9$ represents hydrogen atom or $C_1$-$C_3$ alkoxy group, X represents;

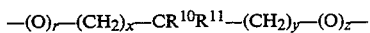
—(O)$_r$—(CH$_2$)$_x$—CR$^{10}$R$^{11}$—(CH$_2$)$_y$—(O)$_z$— in which $R^{10}$ and $R^{11}$ each independently represent hydrogen atom or $C_1$-$C_3$ alkyl group, r and z have the same significance as defined above, and x and y each independently represent an integer from 0 to 3 with the proviso that $0 \leq x+y \leq 3$, or A ring represents:

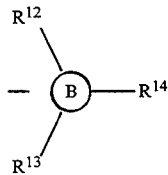

in which B ring represents pyrimidine ring, pyrazole ring or triazole ring, $R^{12}$ and $R^{13}$ each independently represent $C_1$-$C_5$ alkyl group, phenyl group, pyridyl group or $C_1$-$C_5$ alkoxy group, a group:

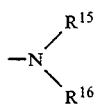

in which $R^{15}$ and $R^{16}$ each independently represent $C_1$-$C_3$ alkyl group, or $R^{15}$ and $R^{16}$, taken together, may form $C_3$-$C_5$ alkylene group, morpholino group or $C_2$-$C_4$ alkoxycarbonyl group, and $R^{14}$ represents hydrogen atom or $C_1$-$C_3$ alkyl group.

In particular, preferred are the compounds wherein m and q each represents 0, n represents 1, p represents 0 or 1, $R^1$ and $R^2$, taken together, represent methylene group, $R^3$ and $R^4$ each represent hydrogen atom, $R^5$ represents pentyl group, and A ring represents

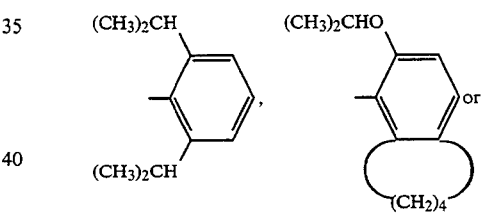

The compounds of the present invention may contain asymmetric carbon in the molecule, and it will be appreciated that such racemic forms as well as optical isomers, thereof are involved within the scope of the present invention.

Illustrative examples of the compounds of the present invention are shown in Tables 1-13. Each symbol in these tables has the following significance.

Me: methyl group, Et: ethyl group, n-Pr: normal propyl group, i-Pr: isopropyl group, n-Bu: normal butyl group, n-Pe: normal pentyl group, n-Hex: normal hexyl group, n-Hep: normal heptyl group, Ph: phenyl group, Pip: piperidino group, the figure in front of a substituent means the substituted position and corresponds to the figure attached to the benzene ring.

TABLE 1

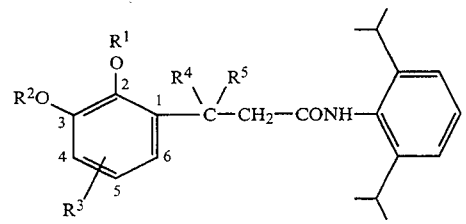

| Compound No. | R¹ | R² | R³ | R⁴ | R⁵ |
|---|---|---|---|---|---|
| 1 | —CH₂— | | —H | —H | -n-Pr |
| 2 | —CH₂— | | —H | —H | -n-Bu |
| 3 | —CH₂— | | —H | —H | -n-Pe |
| 4 | —CH₂— | | —H | —H | -n-Hex |
| 5 | —CH₂— | | —H | —H | -n-Hep |
| 6 | —CH₂— | | —H | —(CH₂)₄— | |
| 7 | —CH₂— | | —H | —(CH₂)₅— | |
| 8 | —CH₂— | | 5-COMe | —H | -n-Pe |
| 9 | —CH₂— | | 5-COEt | —H | -n-Pe |
| 10 | —CH₂— | | 5-COPh | —H | -n-Pe |
| 11 | —CH₂— | | 5-NO2 | —H | -n-Pe |
| 12 | —CH₂— | | 5-NH2 | —H | -n-Pe |
| 13 | —CH₂— | | 5-NMe2 | —H | -n-Pe |
| 14 | —CH₂— | | 5-Pip | —H | -n-Pe |
| 15 | —CH₂— | | 6-NO2 | —H | -n-Pe |
| 16 | —CH₂— | | 6-NMe2 | —H | -n-Pe |
| 17 | —CH₂— | | 5-OH | —H | -n-Pe |
| 18 | —CH₂— | | 5-OMe | —H | -n-Pe |
| 19 | —CH₂— | | 5-OEt | —H | -n-Pe |
| 20 | —CH₂— | | 5-OCOMe | —H | -n-Pe |
| 21 | —CH₂— | | 5-Me | —H | -n-Pe |
| 22 | —CH₂— | | 5-Et | —H | -n-Pe |
| 23 | —CH₂— | | 5-F | —H | -n-Pe |
| 24 | —CH₂— | | 5-Cl | —H | -n-Pe |
| 25 | —CH₂— | | 5-Br | —H | -n-Pe |
| 26 | —Me | —Me | —H | —(CH₂)₄— | |
| 27 | —Me | —Me | —H | —(CH₂)₅— | |
| 28 | —Me | —Me | —H | —H | -n-Bu |
| 29 | —Me | —Me | —H | —H | -n-Pe |
| 30 | —Me | —Me | 5-COMe | —H | -n-Pe |
| 31 | —Me | —Me | 5-COEt | —H | -n-Pe |
| 32 | —Me | —Me | 5-OH | —H | -n-Pe |
| 33 | —Me | —Me | 5-OMe | —H | -n-Pe |
| 34 | —Me | —Me | 5-OCOMe | —H | -n-Pe |
| 35 | —Me | —Me | 5-NMe2 | —H | -n-Pe |
| 36 | —Me | —Me | 5-F | —H | -n-Pe |
| 37 | —Me | —Me | 5-Cl | —H | -n-Pe |
| 38 | —Me | —Me | —H | —H | -n-Hex |
| 39 | —(CH₂)₂— | | —H | —H | -n-Bu |
| 40 | —(CH₂)₂— | | —H | —H | -n-Pe |
| 41 | —(CH₂)₂— | | —H | —H | -n-Hex |
| 42 | —(CH₂)₂— | | —H | —H | —(CH₂)₄— |
| 43 | —(CO₂)₂— | | 5-NME2 | —H | -n-Pe |
| 44 | —Et | —Et | —H | —H | -n-Pe |

TABLE 2

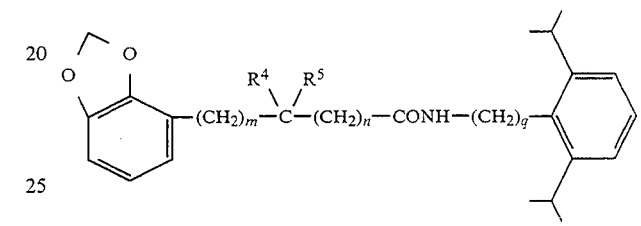

| Compound No. | R⁴ | R⁵ | m | n | q |
|---|---|---|---|---|---|
| 45 | —H | -n-Bu | 1 | 0 | 0 |
| 46 | —H | -n-Pe | 0 | 0 | 0 |
| 47 | —H | -n-Pe | 1 | 0 | 0 |
| 48 | —H | -n-Hex | 1 | 0 | 0 |
| 49 | —H | -n-Pe | 1 | 0 | 1 |
| 50 | —(CH₂)₄— | | 1 | 0 | 0 |
| 51 | —(CH₂)₅— | | 1 | 0 | 0 |
| 52 | —H | -n-Pe | 1 | 1 | 0 |
| 53 | —H | -n-Pe | 1 | 1 | 1 |
| 54 | —H | -n-Pe | 1 | 1 | 2 |
| 55 | —H | -n-Pe | 1 | 2 | 0 |
| 56 | —H | -n-Pe | 2 | 1 | 0 |
| 57 | —H | -n-Pe | 3 | 1 | 0 |
| 58 | —H | -n-Pe | 0 | 0 | 1 |
| 59 | —H | -n-Pe | 0 | 1 | 1 |
| 60 | —H | -n-Pe | 0 | 3 | 0 |
| 61 | —H | -n-Pe | 0 | 3 | 1 |
| 62 | —H | -n-Pe | 1 | 3 | 0 |
| 63 | —H | -n-Pe | 2 | 2 | 0 |
| 64 | —H | -n-Bu | 0 | 2 | 0 |
| 65 | —H | -n-Pe | 0 | 2 | 0 |
| 66 | —H | -n-Hex | 0 | 2 | 0 |

TABLE 3

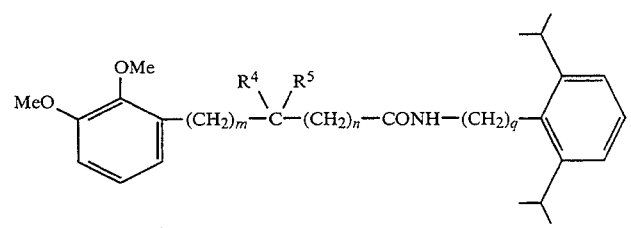

| Compound No. | R⁴ | R⁵ | m | n | q |
|---|---|---|---|---|---|
| 67 | —H | -n-Bu | 1 | 0 | 0 |
| 68 | —H | -n-Pe | 1 | 0 | 0 |
| 69 | —H | -n-Hex | 1 | 0 | 0 |
| 70 | —H | -n-Pe | 1 | 0 | 1 |
| 71 | (CH₂)₄— | | 1 | 0 | 0 |
| 72 | —(CO₂)₅— | | 1 | 0 | 0 |
| 73 | —H | -n-Pe | 1 | 1 | 0 |
| 74 | —H | -n-Pe | 1 | 1 | 1 |
| 75 | —H | -n-Pe | 1 | 1 | 2 |
| 76 | —H | -n-Pe | 1 | 2 | 0 |

TABLE 3-continued

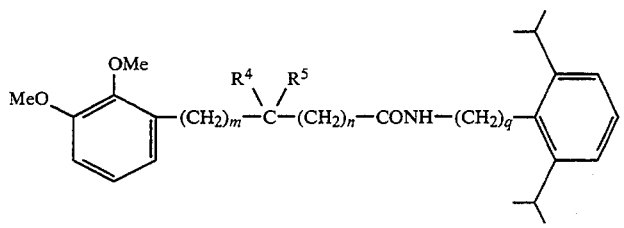

| Compound No. | R⁴ | R⁵ | m | n | q |
|---|---|---|---|---|---|
| 77 | —H | -n-Pe | 2 | 1 | 0 |
| 78 | —H | -n-Pe | 3 | 1 | 0 |
| 79 | —H | -n-Pe | 0 | 3 | 0 |
| 80 | —H | -n-Pe | 0 | 3 | 1 |
| 81 | —H | -n-Pe | 1 | 3 | 0 |
| 82 | —H | -n-Pe | 2 | 2 | 0 |
| 83 | —H | -n-Bu | 0 | 2 | 0 |
| 84 | —H | -n-Pe | 0 | 2 | 0 |
| 85 | —H | -n-Hex | 0 | 2 | 0 |

TABLE 4

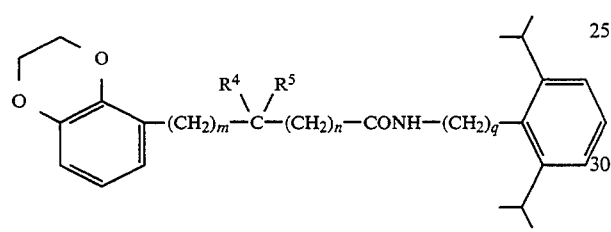

| Compound No. | R⁴ | R⁵ | m | n | q |
|---|---|---|---|---|---|
| 86 | —H | -n-Bu | 0 | 2 | 0 |
| 87 | —H | -n-Pe | 0 | 2 | 0 |
| 88 | —H | -n-Hex | 0 | 2 | 0 |
| 89 | —H | -n-Pe | 1 | 1 | 0 |
| 90 | —H | -n-Pe | 1 | 2 | 0 |
| 91 | —H | -n-Pe | 1 | 1 | 1 |
| 92 | —(CH₂)₄— | | 0 | 2 | 0 |

TABLE 5

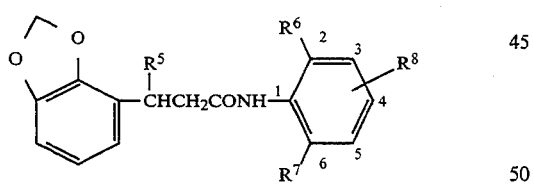

| Compound No. | R⁵ | R⁶ | R⁷ | R⁸ |
|---|---|---|---|---|
| 93 | -n-Pe | -i-Pr | -i-Pr | 3-Me |
| 94 | -n-Pe | -i-Pr | -i-Pr | 4-Et |
| 95 | -n-Pe | -i-Pr | -i-Pr | 3-OMe |
| 96 | -n-Pe | -i-Pr | -i-Pr | 4-OMe |
| 97 | -n-Pe | -i-Pr | -i-Pr | 4-OEt |
| 98 | -n-Pe | -i-Pr | -i-Pr | 3-F |
| 99 | -n-Pe | -i-Pr | -i-Pr | 3-Cl |
| 100 | -n-Pe | -i-Pr | -i-Pr | 4-F |
| 101 | -n-Bn | -i-Pr | -i-Pr | 3-NMe2 |
| 102 | -n-Pe | -i-Pr | -i-Pr | 3-NMe2 |
| 103 | -n-Hex | -i-Pr | -i-Pr | 3-NMe2 |
| 104 | -n-Pe | -i-Pr | -i-Pr | 3-NEt2 |
| 105 | -n-Pe | -i-Pr | -i-Pr | 4-NMe2 |
| 106 | -n-Pe | —OEt | —OEt | —H |
| 107 | -n-Pe | —O-n-Pr | —O-n-Pr | —H |
| 108 | -n-Bu | —O-i-Pr | —O-i-Pr | —H |
| 109 | -n-Pe | —O-i-Pr | —O-i-Pr | —H |
| 110 | -n-Hex | —O-i-Pr | —O-i-Pr | —H |
| 111 | -n-Pe | -OMe | -OMe | 4-OMe |
| 112 | -n-Pe | —OEt | —OEt | 4-OEt |

TABLE 5-continued

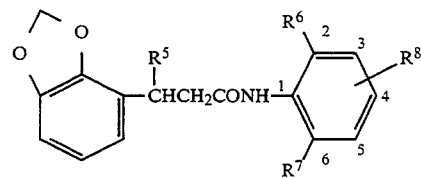

| Compound No. | R⁵ | R⁶ | R⁷ | R⁸ |
|---|---|---|---|---|
| 113 | -n-Bu | —F | —F | —F |
| 114 | -n-Pe | —F | —F | 4-F |
| 115 | -n-Hex | —F | —F | —F |
| 116 | -n-Pe | -ci | -ci | —H |
| 117 | -n-Pe | —Me | —Me | —H |
| 118 | -n-Pe | -Et | -Et | —H |
| 119 | -n-Pe | -n-Pr | -n-Pr | —H |
| 120 | -n-Pe | —Me | —Me | —Me |

TABLE 6

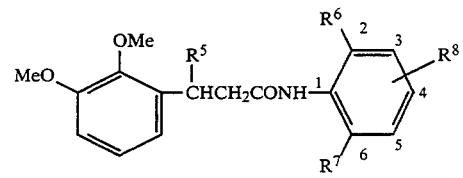

| Compound No. | R⁵ | R⁶ | R⁷ | R⁸ |
|---|---|---|---|---|
| 121 | -n-Pe | -i-Pr | -i-Pr | 3-Me |
| 122 | -n-Pe | -i-Pr | -i-Pr | 4-Et |
| 123 | -n-Pe | -i-Pr | -i-Pr | 3-OMe |
| 124 | -n-Pe | -i-Pr | -i-Pr | 4-OMe |
| 125 | -n-Pe | -i-Pr | -i-Pr | 4-OEt |
| 126 | -n-Pe | -i-Pr | -i-Pr | 3-F |
| 127 | -n-Pe | -i-Pr | -i-Pr | 3-Cl |
| 128 | -n-Pe | -i-Pr | -i-Pr | 4-F |
| 129 | -n-Pe | -i-Pr | -i-Pr | 3-NH₂ |
| 130 | -n-Pe | -i-Pr | -i-Pr | 4-NH₂ |
| 131 | -n-Pe | -i-Pr | -i-Pr | 3-NMe₂ |
| 132 | -n-Pe | -i-Pr | -i-Pr | 4-NMe₂ |
| 133 | -n-Bu | -i-Pr | -i-Pr | 3-NMe₂ |
| 134 | -n-Hex | -i-Pr | -i-Pr | 3-NMe₂ |
| 135 | -n-Pe | -i-Pr | -i-Pr | 3-NEt₂ |
| 136 | -n-Pe | —OEt | —OEt | —H |
| 137 | -n-Pe | —O-n-Pr | —O-n-Pr | —H |
| 138 | -n-Bu | —O-i-Pr | —O-i-Pr | —H |
| 139 | -n-Pe | —O-i-Pr | —O-i-Pr | —H |
| 140 | -n-Hex | —O-i-Pr | —O-i-Pr | —H |
| 141 | -n-Pe | —OEt | —OEt | 4-OEt |
| 142 | -n-Bu | —F | —F | —F |

TABLE 6-continued

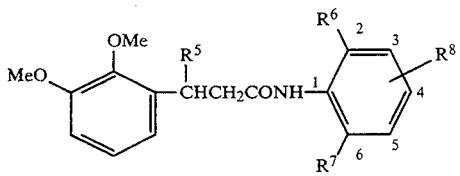

| Compound No. | R⁵ | R⁶ | R⁷ | R⁸ |
|---|---|---|---|---|
| 143 | -n-Hex | —F | —F | —F |
| 144 | -n-Pe | —Cl | —Cl | —F |
| 145 | -n-Pe | —Me | —Me | —H |
| 146 | -n-Pe | —Me | —Me | —Me |
| 147 | -n-Pe | —Et | —Et | —H |

TABLE 6

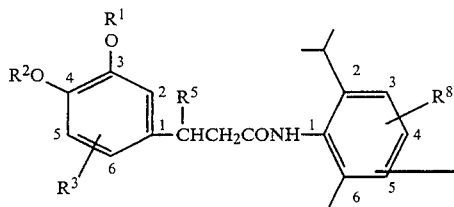

| Compound No. | R¹ | R² | R³ | R⁴ | R⁵ |
|---|---|---|---|---|---|
| 148 | —CH₂— | | —H | -n-Pe | —H |
| 149 | —CH₂— | | —H | -n-Pe | 3-Me |
| 150 | —CH₂— | | —H | -n-Pe | 4-OMe |
| 151 | —CH₂— | | —H | -n-Pe | 3-NMe₂ |
| 152 | —CH₂— | | —H | -n-Pe | 4-NMe₂ |
| 153 | —CH₂— | | 5-OMe | -n-Pe | —H |
| 154 | —CH₂— | | 6-Me | -n-Pe | —H |
| 155 | —CH₂— | | 5-NMe₂ | -n-Pe | —H |
| 156 | —CH₂— | | 5-NMe₂ | -n-Pe | 3-NMe₂ |
| 157 | —CH₂— | | —H | -n-Bu | —H |

TABLE 6-continued

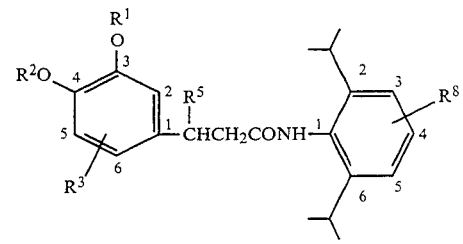

| Compound No. | R¹ | R² | R³ | R⁴ | R⁵ |
|---|---|---|---|---|---|
| 158 | —CH₂— | | —H | -n-Hex | —H |
| 159 | —CH₂CH₂— | | —H | -n-Pe | —H |
| 160 | —CH₂CH₂— | | —H | -n-Pe | 3-NMe₂ |
| 161 | —CH₂CH₂— | 5-OMe | | -n-Pe | —H |
| 162 | —CH₂CH₂— | 5-NMe₂ | | -n-Pe | —H |
| 163 | —Me | —Me | —H | -n-Pe | —H |
| 164 | —Me | —Me | —H | -n-Pe | 3-OMe |
| 165 | —Me | —Me | —H | -n-Pe | 3-NMe₂ |
| 166 | —Me | —Me | —H | -n-Bu | —H |
| 167 | —Me | —Me | —H | -n-Hex | —H |
| 168 | —Me | —Me | 5-NMe₂ | -n-Pe | —H |

TABLE 8

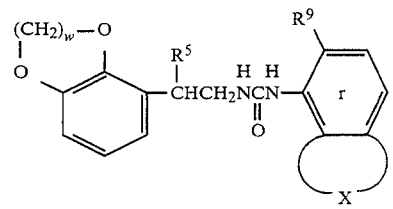

| Compound No. | W | R⁵ | R⁹ | X |
|---|---|---|---|---|
| 169 | 1 | —(CH₂)₄CH₃ | —OCH(CH₃)₂ | (CH₂)₄— |
| 170 | 1 | —(CH₂)₄CH₃ | —OCH(CH₃)₂ | —OCH₂O— |
| 171 | 1 | —(CH₂)₄CH₃ | —OCH(CH₃)₂ | —O(CH₂)₂O— |
| 172 | 1 | —(CH₂)₄CH₃ | —OCH(CH₃)₂ | —O(CH₂)₃O— |
| 173 | 1 | —(CH₂)₄CH₃ | —OCH(CH₃)₂ | —O(CH₂)₂— |
| 174 | 1 | —(CH₂)₄CH₃ | —OCH(CH₃)₂ | —O(CH₂)₃— |
| 175 | 1 | —(CH₂)₄CH₃ | —OCH(CH₃)₂ | —(CH₂)₂O— |
| 176 | 1 | —(CH₂)₄CH₃ | —OCH(CH₃)₂ | —(CH₂)₃O— |
| 177 | 1 | —(CH₂)₄CH₃ | —CH(CH₃)₂ | —OCH₂O— |
| 178 | 1 | —(CH₂)₄CH₃ | —CH(CH₃)₂ | —O(CH₂)₂O— |
| 179 | 1 | —(CH₂)₄CH₃ | —CH(CH₃)₂ | —O(CH₂)₂— |
| 180 | 1 | —(CH₂)₄CH₃ | —CH(CH₃)₂ | —O(CH₂)₃— |
| 181 | 1 | —(CH₂)₄CH₃ | —OCH(CH₃)₂ | —CH(CH₃)(CH₂)₃— |
| 182 | 1 | —(CH₂)₄CH₃ | —OCH(CH₃)₂ | —C(CH₃)₂(CH₂)₃— |
| 183 | 1 | —(CH₂)₄CH₃ | —OCH₃ | —(CH₂)₄— |
| 184 | 1 | —(CH₂)₄CH₃ | —OCH₂CH₃ | —(CH₂)₄— |
| 185 | 1 | —(CH₂)₄CH₃ | —OCH₂CH₃ | —(CH₂)₃— |
| 186 | 1 | —(CH₂)₄CH₃ | —H | —OC(CH₃)₂CH₂— |
| 187 | 1 | —(CH₂)₃OH₃ | —OCH(CH₃)₂ | —(CH₂)₄— |
| 188 | 1 | —(CH₂)₅CH₃ | —OCH(CH₃)₂ | —(CH₂)₄— |
| 189 | 1 | —(CH₂)₄CH₃ | —O(CH₂)₂CH₃ | —(CH₂)₄— |
| 190 | 2 | —(CH₂)₄CH₃ | —OCH(CH₃)₂ | —(CH₂)₄— |
| 191 | 2 | —(CH₂)₄CH₃ | —CH(CH₃)₂ | —O(CH₂)₃— |

TABLE 9

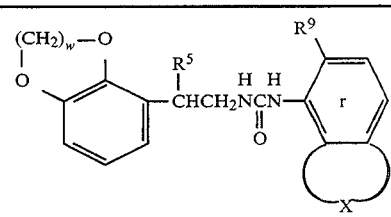

| Compound No. | W | R⁵ | R⁹ | X |
|---|---|---|---|---|
| 192 | 1 | —(CH₂)₄CH₃ | —OCH(CH₃)₂ | —(CH₂)₄— |
| 193 | 1 | —(CH₂)₄CH₃ | —OCH(CH₃)₂ | —(CH₂)₃— |

TABLE 9-continued

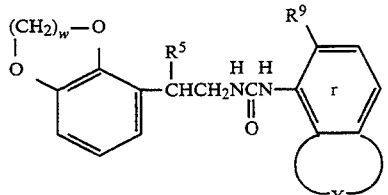

| Compound No. | W | R⁵ | R⁹ | X |
|---|---|---|---|---|
| 194 | 1 | —(CH₂)₄CH₃ | —OCH₂CH₃ | —(CH₂)₄— |
| 195 | 1 | —(CH₂)₄CH₃ | —OCH₃ | —(CH₂)₄— |
| 196 | 1 | —(CH₂)₄CH₃ | —OCH(CH₃)₂ | —OCH₂O— |
| 197 | 1 | —(CH₂)₄CH₃ | —OCH(CH₃)₂ | —O(CH₂)₂O— |
| 198 | 1 | —(CH₂)₄CH₃ | —OCH(CH₃)₂ | —O(CH₂)₃— |
| 199 | 1 | —(CH₂)₄CH₃ | —CH(CH₃)₂ | —O(CH₂)₃— |
| 200 | 1 | —(CH₂)₅CH₃ | —OCH(CH₃)₂ | —(CH₂)₄— |
| 201 | 2 | —(CH₂)₄CH₃ | —OCH(CH₃)₂ | —(CH₂)₄— |
| 202 | 2 | —(CH₂)₄CH₃ | —CH(CH₃)₂ | —(CH₂)₄— |

TABLE 10

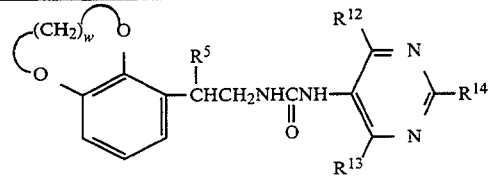

| Compound No. | W | R⁵ | R¹² | R¹³ | R¹⁴ |
|---|---|---|---|---|---|
| 203 | 1 | —CH₂CH₂CH₃ | —N(CH₃)₂ | —N(CH₃)₂ | —H |
| 204 | 1 | —(CH₂)₃CH₃ | —N(CH₃)₂ | —N(CH₃)₂ | —H |
| 205 | 1 | —(CH₂)₅CH₃ | —N(CH₃)₂ | —N(CH₃)₂ | —H |
| 206 | 1 | —(CH₂)₄CH₃ | —N(CH₃)₂ | —N(CH₂CH₃)₂ | —H |
| 207 | 1 | —(CH₂)₄CH₃ | —N(CH₂CH₃)₂ | —N(CH₂CH₃)₂ | —H |
| 208 | 1 | —(CH₂)₄CH₃ | —NHCH(CH₃)₂ | —NHCH(CH₃)₂ | —H |
| 209 | 1 | —(CH₂)₄CH₃ | —N(CH₃)₂ | —OC.H(CH₃)₂ | —H |
| 210 | 1 | —(CH₂)₄CH₃ | —N(CH₃)₂ | —O(CH₂)₂CH₃ | —H |
| 211 | 1 | —(CH₂)₄CH₃ | —O(CH₂)₂CH₃ | —O(CH₂)₂CH₃ | —H |
| 212 | 1 | —(CH₂)₄CH₃ | —CH₃ | —CH₃ | —H |
| 213 | 1 | —(CH₂)₄CH₃ | —CH₂CH₃ | —CH₂CH₃ | —H |
| 214 | 1 | —(CH₂)₄CH₃ | —CH(CH₃)₂ | —CH(CH₃)₂ | —H |
| 215 | 1 | —(CH₂)₄CH₃ | —N(CH₃)₂ | —N(CH₃)₂ | —CH₃ |
| 216 | 1 | —(CH₂)₄CH₃ | —N(CH₃)₂ | —N(CH₃)₂ | |
| 217 | 1 | —(CH₂)₄CH₃ | pyrrolidinyl | pyrrolidinyl | —H |
| 218 | 1 | —(CH₂)₄CH₃ | morpholinyl | morpholinyl | —H |
| 219 | 1 | —(CH₂)₄CH₃ | —OCH₃ | —OCH₃ | —H |
| 220 | 1 | —(CH₂)₄CH₃ | —OCH(CH₃)₂ | —OCH(CH₃)₂ | —H |
| 221 | 1 | —(CH₂)₄CH₃ | —N(CH₃)₂ | —OCH₂CH₃ | —H |
| 222 | 2 | —(CH₂)₄CH₃ | —N(CH₃)₂ | —N(CH₃)₂ | —H |
| 223 | 2 | —(CH₂)₄CH₃ | —N(CH₃)₂ | —OCH₂CH₃ | |
| 224 | 2 | —(CH₂)₄CH₃ | N(CH₃)₂ | —OCH(CH₃)₂ | |

TABLE 11

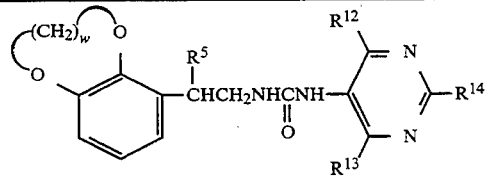

| Compound No. | W | R⁵ | R¹² | R¹³ | R¹⁴ |
|---|---|---|---|---|---|
| 225 | 1 | —(CH₂)₃CH₃ | —N(CH₃)₂ | —N(CH₃)₂ | —H |
| 226 | 1 | —(CH₂)₄CH₃ | —N(CH₃)₂ | —N(CH₃)₂ | —H |
| 227 | 1 | —(CH₂)₅CH₃ | —N(CH₃)₂ | —N(CH₃)₂ | —H |
| 228 | 1 | —(CH₂)₄CH₃ | —N(CH₃)₂ | —N(CH₂CH₃)₂ | —H |
| 229 | 1 | —(CH₂)₄CH₃ | —N(CH₂CH₃)₂ | —N(CH₂CH₃)₂ | —H |
| 230 | 1 | —(CH₂)₄CH₃ | —NHCH(CH₃)₂ | —NHCH(CH₃)₂ | —H |
| 231 | 1 | —(CH₂)₄CH₃ | —N(CH₃)₂ | —OCH(CH₃)₂ | —H |
| 232 | 1 | —(CH₂)₄CH₃ | —N(CH₃)₂ | —OCH₂CH₂CH₃ | —H |
| 233 | 1 | —(CH₂)₄CH₃ | —OCH₂CH₂CH₃ | —OCH₂CH₂CH₃ | —H |
| 234 | 1 | —(CH₂)₄CH₃ | —CH₃ | —CH₃ | —H |
| 235 | 1 | —(CH₂)₄CH₃ | —CH₂CH₃ | —CH₂CH₃ | —H |

TABLE 11-continued

| Compound No. | W | R⁵ | R¹² | R¹³ | R¹⁴ |
|---|---|---|---|---|---|
| 236 | 1 | —(CH₂)₄CH₃ | —CH(CH₃)₂ | —CH(CH₃)₂ | —H |
| 237 | 1 | —(CH₂)₄CH₃ | —N(CH₃)₂ | —N(CH₃)₂ | —CH₃ |
| 238 | 2 | —(CH₂)₄CH₃ | —N(CH₃)₂ | —N(CH₃)₂ | —H |
| 239 | 2 | —(CH₂)₄CH₃ | —N(CH₃)₂ | —OCH CH₃ | —H |
| 240 | 2 | —(CH₂)₄CH₃ | —N(CH₃)₂ | —OCH (CH₃) 2 | —H |

TABLE 12

| Compound No. | W | R⁵ | R¹² | R¹³ | R¹⁴ |
|---|---|---|---|---|---|
| 241 | 1 | —(CH₂)₄CH₃ | —CH(CH₃)₂ | —C(CH₃)3 | —H |
| 242 | 1 | —(CH₂)₄CH₃ | —CH(CH₃)₂ | —C₆H₅ | —H |
| 243 | 1 | —(CH₂)₄CH₃ | —CH(CH₃)₂ | —C₆H₅ | —CH₃ |
| 244 | 1 | —(CH₂)₄CH₃ | —C₆H₅ | —CH₃ | —H |
| 245 | 1 | —(CH₂)₄CH₃ | —OCH₃ | —CH₃ | —H |
| 246 | 1 | —(CH₂)₄CH₃ | —OCH₂CH₂CH₃ | —CH(CH₃)₂ | —H |
| 247 | 1 | —(CH₂)₄CH₃ | —N(CH₃)₂ | —CH(CH₃)₂ | —H |
| 248 | 1 | —(CH₂)₄CH₃ | —OCH(CH₃)₂ | —C₆H₅ | —CH₃ |
| 249 | 1 | —(CH₂)₄CH₃ | —OCH(CH₃)₂ | —CH₃ | —CH₃ |
| 250 | 1 | —(CH₂)₄CH₃ | —OCH(CH₃)₂ | —CH(CH₃) 2 | —CH₃ |
| 251 | 1 | —(CH₂)₄CH₃ | —OCH(CH₃)₂ | —C(CH₃)3 | —CH₃ |
| 252 | 1 | —(CH₂)₄CH₃ | —COOCH₂CH₃ | —C₆H₅ | —H |
| 253 | 1 | —(CH₂)₄CH₃ | —OCH(CH₃)₂ | —CH(CH₃)₂ | —CH₂CH₃ |
| 254 | 1 | —(CH₂)₃CH₃ | —OCH(CH₃)₂ | —C(CH₃)3 | —CH₃ |
| 255 | 1 | —(CH₂)₅CH₃ | —OCH(CH₃)₂ | —C(CH₃)3 | —CH₃ |
| 256 | 2 | —(CH₂)₄CH₃ | —OCH(CH₃)₂ | —C(CH₃)3 | —CH₃ |

TABLE 13

[Structure: benzodioxole-phenyl-CH(CH₂)₄CH₃-CH₂NHC(O)NH-B ring with R¹², R¹³, R¹⁴ substituents]

| Compound No. | B | R² | R³ | R¹⁴ |
|---|---|---|---|---|
| 257 | -N (pyrrole, N-linked) | 2-CH(CH₃)₂ | 5-CH(CH₃)₂ | —H |
| 258 | -N (pyrrole, N-linked) | 2-CH(CH₃)₂ | 5-OCH(CH₃)₂ | —H |
| 259 | -N (pyrrole, N-linked) | 2-OCH(CH₃)₂ | 5-OCH(CH₃)₂ | —H |
| 260 | -N (pyrrole, N-linked) | 2-N(CH₃)₂ | 5-N(CH₃)₂ | —H |
| 261 | pyrrole (C-linked, N in ring) | 1-CH(CH₃)₂ | 3-CH(CH₃)₂ | —H |
| 262 | pyrrole (C-linked) | 1-CH(CH₃)₂ | 3-OCH(CH₃)₂ | —H |
| 263 | pyrrole (C-linked) | 1-CH(CH₃)₂ | 3-N(CH₃)₂ | —H |
| 264 | pyrrole (C-linked) | 2-CH(CH₃)₂ | 4-CH(CH₃)₂ | —H |
| 265 | pyrrole (C-linked) | 2-N(CH₃)₂ | 4-N(CH₃)₂ | —H |
| 266 | imidazole (N-linked) | 2-CH(CH₃)₂ | 5-CH(CH₃)₂ | —H |
| 267 | imidazole (N-linked) | 2-OCH₂CH₂CH₃ | 5-CH(CH₃)₂ | —H |
| 268 | imidazole (N-linked) | 2-NHCH₂CH₃ | 5-CH(CH₃)₂ | —H |
| 269 | imidazole (N-linked) | 2-N(CH₃)₂ | 5-N(CH₃)₂ | —H |

TABLE 13-continued

[Structure: benzodioxole with (CH2)4CH3 and CHCH2NHCNH-B-R14 side chain, with R12, R13 substituents on ring B]

| Compound No. | B | R² | R³ | R¹⁴ |
|---|---|---|---|---|
| 270 | pyrazine | 3-CH(CH₃)₂ | 5-CH(CH₃)₂ | —H |
| 271 | pyrazine | 3-CH(CH₃)₂ | 5-N(CH₃)₂ | —H |
| 272 | pyridazine | 3-CH(CH₃)₂ | 5-CH(CH₃)₂ | —H |
| 273 | pyridazine | 3-N(CH₃)₂ | 5-CH(CH₃)₂ | —H |
| 274 | pyridazine | 3-OCH(CH₃)₂ | 5-CH(CH₃)₂ | —H |
| 275 | pyridine | 2-CH(CH₃)₂ | 4-CH(CH₃)₂ | —H |
| 276 | pyridine | 2-OCH(CH₃)₂ | 4-CH(CH₃)₂ | —H |
| 277 | pyridine | 2-OCH(CH₃)₂ | 4-OCH(CH₃)₂ | —H |
| 278 | pyridine | 2-N(CH₃)₂ | 4-CH(CH₃)₂ | —H |
| 279 | pyridine | 2-N(CH₃)₂ | 4-N(CH₃)₂ | —H |
| 280 | pyridine | 2-N(CH₃)₂ | 4-N(CH₃)₂ | 6-CH₃ |
| 281 | pyridine (4-yl) | 3-CH(CH₃)₂ | 5-CH(CH₃)₂ | —H |

TABLE 13-continued
Structure: benzodioxole-CH(CH2)4CH3-CH2NHC(O)NH-B(R12,R13)-R14
| Compound No. | B | R2 | R3 | R14 |
|---|---|---|---|---|
| 282 | 4-pyridyl | 3-OCH(CH3)2 | 5-CH(CH3)2 | —H |
| 283 | 4-pyridyl | 3-OCH(CH3)2 | 5-OCH(CH3)2 | —H |
| 284 | 4-pyridyl | 3-N(CH3)2 | 5-CH(CH3)2 | —H |
| 285 | 4-pyridyl | 3-N(CH3)2 | 5-N(CH3)2 | —H |
| 286 | 4-pyridazinyl | 3-CH(CH3)2 | 5-CH(CH3)2 | —H |
| 287 | 4-pyridazinyl | 3-N(CH3)2 | 5-N(CH3)2 | —H |
| 288 | 1,2,4-triazol-1-yl | 3-(2-pyridyl) | 3-(2-pyridyl) | —H |
Synthesis of the compounds of the present invention will be explained below.
(i) Compounds of p=0:
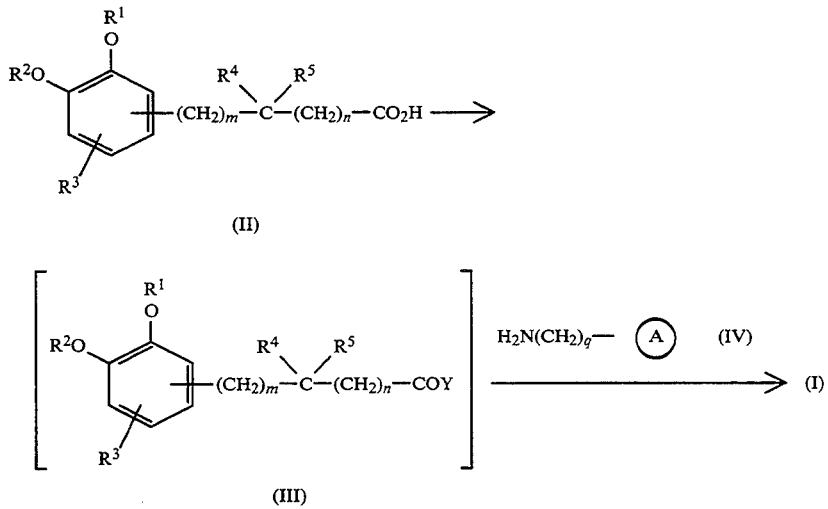

In the formulae above, $R^1$, $R^2$, $R^3$, $R^4$, $R^5$, m, n, q, and A ring have the same significance as defined above, and Y represents a leaving group such as halogen atom, alkyloxycarbonyloxy group, pivaloyloxy group, dichlorophosphoryloxy group (—OP(O)Cl$_2$), phthalimidoxy group, succinimidoxy group, 1-imidazolyl group, alkyloxy group or the like.

Compound (I) of the present invention can be prepared by converting the phenylalkylcarboxylic acid derivative (II) to the intermediate (III) and reacting it with Compound (IV).

As the intermediate (III) there are exemplified phenylalkylcarboxylic acid chloride (in the formula above, Y represents chlorine atom) obtained by reacting phenylalkylcarboxylic acid derivative (II) with thionyl chloride, phosphorus pentachloride, phosphorus trichloride or the like; mixed acid anhydride (in the formula, Y represents alkyloxycarbonyoloxy group or pivaloyloxy group) obtained by reacting phenylalkylcarboxylic acid (II) with alkyl chloroformate or pivaolyl chloride; acid anhydride (in the formula, Y represents dichlorophosphoryloxy group) obtained by reacting phenylalkylcarboxylic acid (II) with phosphoryl chloride; active ester (in the formula, Y represents phthalimidoxy group or succinimidoxy group) obtained by reacting phenylalkylcarboxylic acid (II) with N-hydroxyphthalimide or N-hydroxysuccinimide; N-acylderivative (in the formula, Y represents 1-imidazolyl group) obtained by reacting phenylalkylcarboxylic acid (II) with carbonyl diimidazole; ester derivative (in the formula, Y represents alkyloxy group) obtained by reacting phenylalkylcarboxylic acid (II) with ordinary alcohol, and the like. In the reactions above, inert solvents such as methylene chloride, chloroform, 1, 2-dichloroethane, benzene, toluene, hexane, heptane, diethyl ether, tetrahydrofuran, dioxane, ethyl acetate, N,N-dimethylformamide and the like may be used as a solvent.

Further, inert organic amines such as triethylamine, pyridine, etc. or inorganic bases such as sodium hydrogencarbonate, potassium carbonate, etc. can be used for effecting the reactions smoothly. The reactions are effected at temperature from −15°–100° C. preferably 0° C.-80° C.

The stating phenylalkylcarboxylic acid (II) (n=0) can be prepared in the same manner as described, for example, in J-P. Pieu et al., Tetrahedron, 1986, 4095. The compound (n=1–3) can be prepared by adding 1–3 carbon atoms to the phenylalkylcarboxylic acid (n=0). These reactions can be effected, for example, according to Shin Zikken Kagaku Koza Vol.14, Synthesis and Reactions of Organic Compounds (II), p. 921, edited by Chemical Society of Japan, (1977), published by Maruzen.

For example, phenylalkylcarboxylic acid (n=1) can be prepared by reducing phenylalkylcarboxylic acid (n=0), for example, with lithium aluminum hydride (LiAlH$_4$) to give phenylalkyl alcohol derivative, converting the latter into the methanesulfonic acid ester with methanesulfonyl chloride or converting the same into phenylalklyl halide with phosphorus halide or the like, reacting said product with sodium cyanide or the like to give the phenylalkyl cyanide and hydrolyzing the cyanide with an acid or an alkali.

The starting compound (IV) (q=0) is known or can be easily prepared by known methods. The compound (q=1–3) can be prepared by adding 1–3 carbon atoms to the carboxylic acid derivative or its halide derivative. These reactions can be effected according to the method as described, for example, in Shin Jikken Kagaku Koza, Vol. 14, Synthesis and Reactions of Organic Compound (III), p. 1332, edited by Chemical Society of Japan (1978), published by Maruzen.

(ii) Compounds of p=1:

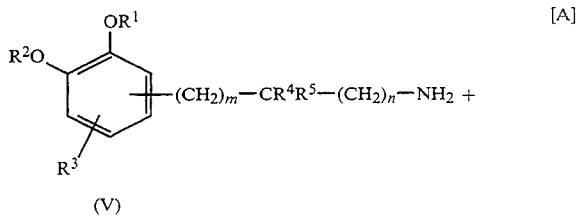

[A]

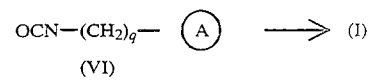

In the formulae, $R^1$, $R^2$, $R^3$, $R^4$, $R^5$, m, n, q, and A ring have the same significance as defined above.

The compound (I) of the present invention can be prepared by condensing the compound (V) with the compound (VI) in an inert solvent such as benzene, toluene, xylene, hexane, heptane, diethyl ether, tetrahydrofuran (THF), dioxane, N, N-dimethylformamide or the like at temperature from 0° C. to 150° C.

The compound (VI) above can be prepared by reacting the compound of the general formula (VII):

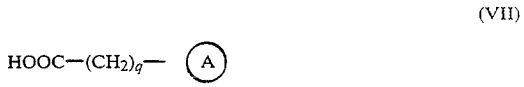

(VII)

wherein q and A ring have the same significance as defined above, with diphenylphosphoryl azide (DPPA) in the presence of inert organic amine such as triethylamine or the like at temperature from room temperature to 150° C. in an inert solvent such as benzene, toluene, xylene or the like.

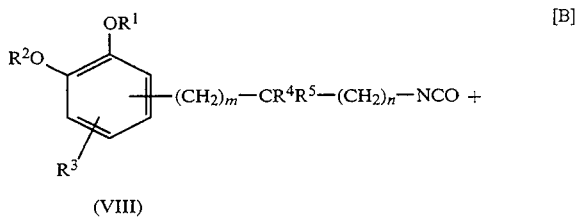

[B]

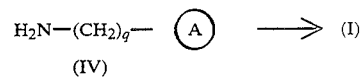

wherein $R^1$, $R^2$, $R^3$, $R^4$, $R^5$, m, n, q, and A ring have the same significance as defined above.

The compound (I) of the present invention can be prepared by reacting the compound (VIII) with the compound (IV) under the same conditions as in A method above.

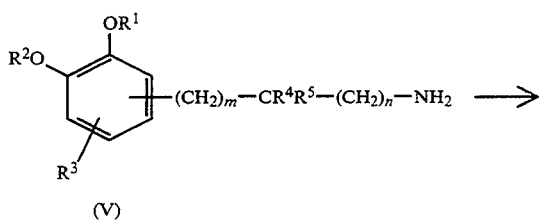

(V)

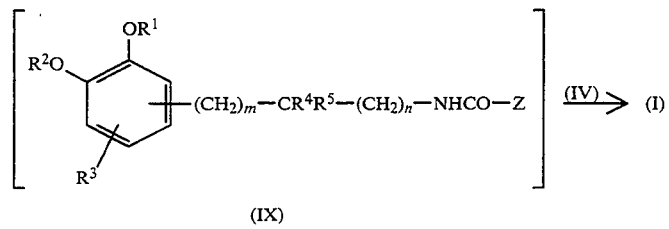

In the formulae above, $R^1$, $R^2$, $R^3$, $R^4$, $R^5$, m, n, and q have the same significance as defined above and Z represents a leaving group such as halogen atom, aryloxy group, alkyloxy group or the like.

The compound (I) of the present invention can be prepared by converting the compound (V) into the intermediate (IX) and reacting the latter with the compound (IV). The intermediate (IX) illustratively includes phenylalkylcarbamoyl chloride (IX, Z=Cl) obtained by reacting the compound (V) with phosgene, trichloromethyl chloroformate, bis (trichloromethyl) carbonate or the like, phenylalkylcarbamoyl aryl ester or phenylalkylcarbamoyl alkyl ester (IX, Z=aryloxy or alkyloxy group) obtained by reacting the compound (V) with aryl chloroformate or alkyl chloroformate. In this reaction, any solvents inert to the reaction such as benzene, toluene, hexane, heptane, diethyl ether, tetrahydrofuran, dioxane, ethyl acetate or the like may be used without special limitation. Further, organic amines such as triethylamine, pyridine or the like and inorganic bases such as sodium hydrogencarbonate, potassium carbonate or the like which are inert to the reaction may be used for effecting the reaction smoothly, and the reaction is effected at temperature from −15° C. to 150° C., preferably 0° C. to 120° C.

[D]

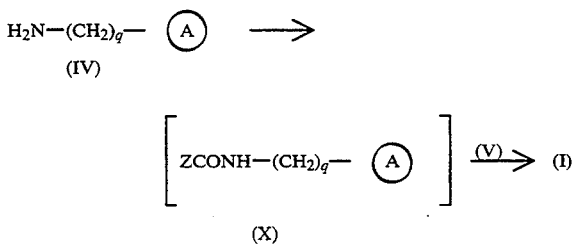

In the above formulae, q, A ring and Z have the same significance as defined above.

The compound (I) of the present invention can be prepared by converting the compound (IV) into the intermediate (X) and reacting the latter with the compound (V).

The intermediate (X) above illustratively includes phenylcarbamoyl chloride (X, Z=Cl) obtained by reacting the compound (IV) with phosgene, trichloromethyl chloroformate, bis(trichloromethyl) carbonate or the like and phenylcarbamoyl aryl ester or phenylcarbamoyl alkyl ester (X, Z=aryloxy or alkyloxy group) obtained by reacting the compound (IV) with aryl or alkyl chloroformate. The reaction is effected under the same conditions as in C method above.

The compound (V) used as a starting material in A-D methods can be prepared as shown below.

Scheme 1:

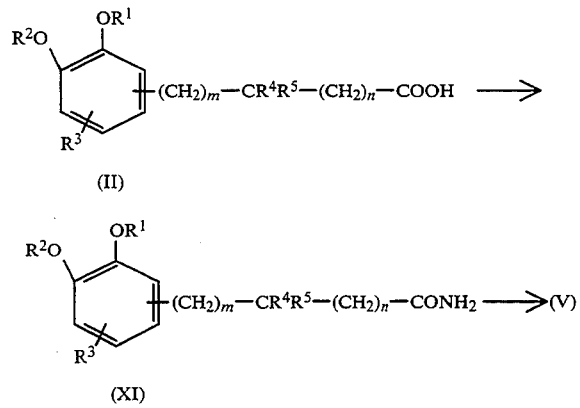

In the formulae above, $R^1$, $R^2$, $R^3$, $R^4$, $R^5$, m and n have the same significance as defined above.

For example, the compound (V) is prepared by reacting phenylalkylcarboxylic acid derivative (II), obtained according to the method as described in J-P. Pieu et al, Tetrahedron, 1986, 4095, with thionyl chloride to give the acid chloride and treating the latter with ammonia to give phenylalkylcarbamide derivative (XI) and then reducing the intermediate (XI) with a reducing agent such as lithium aluminum hydride (LiAlH$_4$) or sodium borohydride-acetic acid, or according to the method shown in the following scheme 2.

Scheme 2:

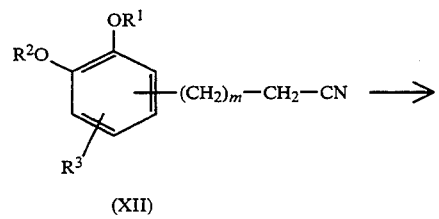

-continued

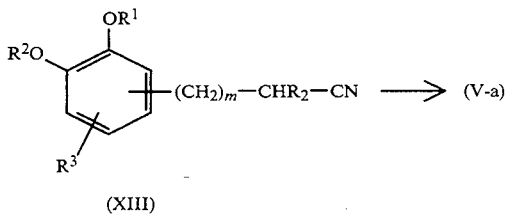

(XIII)

In the fomulae above, $R^1$, $R^2$, $R^3$, $R^5$, and m have the same significance as defined above, and the compound (V-a) means the compound (V)($R^4$=H; n=1).

Thus, the compound (XII) is alkylated at α-hydrogen position of the nitrile, for example, according to the method as described in Shinjikken Kagaku Koza Vol. 14, Synthesis and Reactions of Organic Compounds (III), p.1447 (1978), edited by Chemical Society of Japan, published by Maruzen, to give the compound (XIII), and the latter is reduced with a reducing agent such as LiAlH₄ or the like to give the aimed compound.

Optically active compound (V) can be prepared by treating racemic phenylalkylcarboxylic acid derivative (II) with optically active amine such as (R)- or (S)-1-phenylethylamine or the like to make a salt and recrystallizing the salt or by treating racemic compound (V) with optically active carboxylic acid such as D- or L-tartaric acid to give a salt and recrystallizing the salt.

Of the starting materials, namely the compound (IV) and the compound (VII), the compound (q=0) is known or easily available according to known methods. The compound (q=1-3) can be prepared by increasing 1-3 carbon atoms to the carboxylic acid derivative or halide derivative. These reactions are effected according to the method as described in Shinjikken Kagaku Koza, Vol. 14, Synthesis and Reactions of Organic Compound (III), p.1332 (1978), edited by Chemical Society of Japan, published by Maruzen.

The compounds of the present invention are useful as medicinals for treating hyperlipemia or atherosclerosis, and they are preferably orally administered. Appropriate formulations for oral administration are tablets, granules, powders, capsules or the like. The formulations may be prepared by mixing the compound of the present invention with usual additives such as excipients (e, g, glucose, lactose, corn starch or mannitol), binders (e, g, hydroxypropyl cellulose (HPC), carboxymethyl cellulose (CMC), etc.), disintegrators (e, g, starch, gelatin powder, etc.), lubricants (e, g, talc, magnesium stearate, etc.).

Appropriate daily dosage of the compound of the present invention to human adult by oral route is 0.1 mg to 300 mg. However, the specific dosage used may vary, depending upon necessity of the patient, degree of diseases to be treated, activity degree of the effective compound.

EXAMPLES

The present invention will be explained in more detail below by the examples, but the scope of the present invention should not be limited by these examples unless it exceeds the gist of the present invention.

Reference Example 1

Preparation of 3-(2, 3-methylenedioxyphenyl)octanoic acid

To a suspension of 1.26 g (33 mmol) of lithium aluminum hydride (LiAlH₄) in 50 ml of tetrahydrofuran (THF) was dropwise added 5.01 g (20 mmol) of 2-(2, 3-methylenedioxyphenyl)heptanoic acid under water cooling. The reaction mixture was stirred at room temperature for 3 hours, and 1.26 ml of water, 1.26 ml of 15% aqueous sodium hydroxide and 3.78 ml of water were added in this order. After 50 ml of ethyl ether was added, the mixture was stirred, and precipitated white solid was filtered off. The filtrate was concentrated in vacuo to give 4.65 g of 2-(2, 3-methylenedioxyphenyl)-heptanol as an oil.

To a solution of 6.65 g (28.1 mmol) of 2-(2, 3-methylenedioxyphenyl)heptanol in 80 ml of methylene chloride was added 4.30 ml (30.9 mmol) of triethylamine, and 2.28 ml (29.5 mmol) of methanesulfonyl chloride was dropwise added. The reaction mixture was stirred at room temperature for 30 minutes, washed with water twice, dried over anhydrous magnesium sulfate and the solvent was evaporated to give 8.76 g of 2-(2, 3-methylenedioxyphenyl)heptyl methanesulfonate as an oil.

Thus obtained 8.76 g (27.9 mmol) of 2-(2, 3-methylenedioxyphenyl)heptyl methanesulfonate was dissolved in 70 ml of methyl ethyl ketone, and the solution was mixed with 6.6 g of sodium iodide. The resultant mixture was refluxed under heating for 10 hours. After cooling, the precipitated salt was filtered off, and the filtrate was concentrated in vacuo. The residue was chromatographed on a silica gel column (eluent; ethyl acetate/hexane=1/20) to give 8.36 g of 2-(2, 3-methylenedioxyphenyl)heptyl iodide as an oil.

Then, 8.36 g (24.1 mmol) of 2-(2, 3-methylenedeoxyphenyl)heptyl iodide was dissolved in 25 ml of dimethyl sulfoxide, and the solution was mixed with 1.42 g (29 mmol) of sodium cyanide. The resultant mixture was stirred under heating at 100° C. for 3 hours. After cooling, the mixture was mixed with 75 ml of water and extracted twice with ethyl acetate. The extract was washed with saturated saline, dried over anhydrous magnesium sulfate, and the solvent was evaporated. The residue was chromatographed on a column of silica gel, eluting with ethyl acetate/hexane (1/10) to give 3.00 g of 2-(2, 3-methylenedioxyphenyl)heptyl cyanide as an oil.

To 3.00 g (12.2 mmol) of 2-(2, 3-methylenedioxyphenyl)heptyl cyanide were added 18 ml of ethylene glycol, 6 ml of water and 3.65 g (purity 85% 55.3 mmol) of potassium hydroxide, and the resultant mixture was refluxed under heating for 3.hours. After cooling, the mixture was mixed with 60 ml of water and acidified with hydrochloric acid and extracted twice with ethyl acetate.

The extract was washed with saturated saline, and the solvent was evaporated, The residue was chromatographed on a silica gel column, eluting with ethyl acetate/hexane (1:2) to give 2.64 g of 3-(2, 3-methylenedioxyphenyl)octanoic acid as an oil.

¹H NMR (CDCl₃): δ=0.83 (t, 3H), 1.1–1.3 (m, 6H), 1.57–1.70 (m, 2H), 2.61–2.78 (m, 2H), 3.12–3.24 (m, 1H), 5.91 (s, 2H), 6.63–6.79 (m, 3H).

Reference Example 2

Preparation of (R)-2-(2, 3-methylenedioxyphenyl)heptanoic acid

The salt obtained from (±)-2-(2, 3-methylenedioxyphenyl)heptanoic acid and (S)-1-phenylethylamine was recrystallized three times from a mixed solvent of ethyl acetate-heptane (1:9). This salt was mixed with hydrochloric acid and shaken with methylene chloride. The organic layer was washed with dilute hydrochloric acid, dried over anhydrous magneisum sulfate and the solvent was evaporated to give (R)-2-(2, 3-methylenedioxyphenyl)heptanoic acid. Yield 39%, mp, 47°–48° C., $[\alpha]_D^{25}$ −64.5° (MeOH, c=1.01).

Reference Example 3

Using various carboxylic acids in place of 2-(2, 3-methylenedioxyphenyl)heptanoic acid in Reference Example 1, the following carboxylic acids having one carbon atom increased were prepared in the same manner as in Reference Example 1.
3-(2, 3-dimethoxyphenyl)octanoic acid
3-(2, 3-dimethoxyphenyl)heptanoic acid
3-(2, 3-dimethoxyphenyl)nonanoic acid
(R)-3-(2, 3-methylenedioxyphenyl)octanoic acid
(S)-3-(2, 3-methylenedioxyphenyl)octanoic acid
(S)-3-(2, 3-dimethoxyphenyl)octanoic acid

Reference Example 4

Preparation of 4-(2, 3-methylenedioxyphenyl)nonanoic acid

To a suspension of 0.40 g of sodium hydride (60% oil dispersion, 10 mmol) in 10 ml of N,N-dimethylformamide was dropwise added 1.60 g (10 mmol) of diethyl malonate under ice cooling, and the resultant mixture was stirred for 30 minutes. To this mixture were added a solution of 3.14 g (10 mmol) of 2-(2, 3-methylenedioxyphenyl)heptyl methanesulfonate, intermediate in Reference Example 1. in 6 ml of N,N-dimethylformamide and 1.50 g (10 mmol) of sodium iodide, and the mixture was stirred at 100° C. for 2 hours. After cooling, the mixture was mixed with water and shaken with ethyl acetate. The extract was washed with saturated saline, dried over anhydrous magnesium sulfate and the solvent was evaporated in vacuo. The residue was chromatographed on a column of silica gel, eluting with ethyl acetate/hexane (1/10) to give 1.49 g of 2-(2, 3-methylenedioxyphenyl)heptylmalonic acid diethyl ester as an oil.

To a solution of 1.49 g (3.94 mmol) of 2-(2, 3-methylenedioxyphenyl)heptylmalonic acid diethylester in 10 ml of ethanol was added 6.6 g of 10% aqueous sodium hydroxide, and the resultant mixture was refluxed under heating for 2.5 hours. The reaction mixture was concentrated in vacuo, mixed with 5 ml of water and 0.8 ml of conc. sulfuric acid and refluxed under heating for 4 hours. After cooling, the reaction mixture was shaken with ethyl acetate, and the extract was washed with saturated saline, dried over anhydrous magnesium sulfate and the solvent evaporated. The residue was chromatographed on a silica gel column, eluting with ethyl acetate/hexane (1/2) to give 0.92 g of 4-(2, 3-methylenedioxyphenyl) nonanoic acid as an oil.

$^1$H NMR(CDCl$_3$): δ=0.84 (t, 3H), 1.05–1.30 (m, 6H), 1.55–1.70 (m, 2H), 1.85–2.07 (m, 2H), 2.19–2.26 (m, 2H), 2.66–2.78 (m, 1H), 5.91 (s, 2H), 6.60–6.80 (m, 3H).

Reference Example 5

Preparation of 4-(2, 3-dimethoxyphenyl)nonanoic acid

Using 2-(2, 3-dimethoxyphenyl)heptyl methanesulfonate in place of 2-(2, 3-methylenedioxyphenyl)heptyl methanesulfonate in Reference Example 4, 4-(2, 3-dimethoxyphenyl)nonanoic acid was prepared in the same manner as in Reference Example 4.

Reference Example 6

Preparation of 3-(5-acetyl-2, 3-dimethoxyphenyl) octanoic acid

To a solution of 800 mg (6.00 mmol) of anhydrous aluminum chloride in 5 ml of methylene chloride were added 0.43 g (6.05 mmol) of acetyl chloride with stirring and ice cooling and then dropwise a solution of 925 mg (3.00 mmol) of 3-(2, 3-dimethoxyphenyl)octanoic acid ethyl ester in 3 ml of methylene chloride. The resultant mixture was allowed to react under ice cooling for 20 minutes and added portionwise into ice water. The organic layer was separated, and the aqueous layer was extracted with methylene chloride. The organic layers were combined, washed with water and aqueous saturated sodium hydrogencarbonate, dried over anhydrous magnesium sulfate and the solvent evaporated in vacuo. The residue was chromatographed on a silica gel column, eluting with ethyl acetate/hexane (1/5) to give 900 mg of 3-(5-acetyl-2, 3-dimethoxyphenyl)octanoic acid ethyl ester as a colorless oil. Yield, 86%.

$^1$H NMR (CDCl$_3$): δ=0.83 (3H, t), 1.14 (3H, t), 1.22 (6H, m), 1.62 (2H, m), 2.58 (3H, s), 2.64 (2H, m), 3.56 (1H, m), 3.91 (6H, s), 4.04 (2H, q), 7.40 (2H, m).

To a solution of 890 mg (2.54 mmol) of the oil obtained above in 10 ml of ethanol was added 3 ml of aqueous sulution of 95% sodium hydroxide (180 mg, 4.27 mmol), and the resultant mixture was refluxed with heating for 1 hour. The ethanol was evaporated in vacuo, and the remaining aqueous solution was acidified with dilute hydrochloric acid and shaken with ethyl acetate. The organic layer was washed with water, dried over anhydrous magnesium sulfate and the solvent evaporated in vacuo to give 820 mg of the titled 3-(5-acetyl-2, 3-dimethoxyphenyl)octanoic acid. Yield 100%.

Reference Example 7

Preparation of 2-(2, 3-dimethoxybenzyl)heptanoic acid

To a suspension of 60% sodium hydride (440 mg, 11 mmol) in 5 ml of dimethylformamide was added a solution of 2.30 g (10 mmol) of n-pentylmalonic acid diethyl ester in 5 m of dimethylformamide under stirring and ice cooling, and the resultant mixture was stirred for 30 minutes. A solution of 1.86 g (10 mmol) of 2, 3-dimethoxybenzyl chloride in 5 ml of dimethylformamide was dropwise added to the mixture, which was stirred at 70° C. for 1 hour. After cooling, the reaction mixture was mixed with water and extracted with ethyl acetate. The organic layers were combined, washed with water and saturated saline in this order, dried over anhydrous magnesium sulfate and the solvent evaporated in vacuo. The residue was chromatographed on a silica gel column, eluting with ethyl acetate/hexane (1/12) to give 2.78 g of 2, 3-dimethoxybenzyl-n-pentylmalonic acid diethyl ester as a colorless oil. Yield, 73%.

To a solution of 2.77 g (7.28 mmol) of the oil obtained above in 20 ml of ethanol was added 10 ml of aqueous solution of 95% sodium hydroxide (1.25 g, 29.7 mmol), and the resultant mixture was refluxed under heating at 100° C. for 4 hours. Working up as usual gave 1.54 g of the half ester in which one of two ethyl ester groups had been hydrolyzed. Yield, 75%. This half ester (560 mg) was collected, mixed with 4 ml of ethylene glycol and 2 ml of water, then 85% potassium hydroxide (500 mg), and the resultant mixture was allowed to react on an oil bath heated at 150° C. for 4 hours. After cooling, the mixture was mixed with water, acidified with hydrochloric acid and shaken with ethyl acetate. The extract was washed with water and saturated saline and dried over anhydrous magnesium sulfate and the solvent evaporated in vacuo to give 430 mg of the titled 2-(2, 3-dimethoxybenzyl) heptanoic acid as a colorless oil.

$^1$H NMR (CDCl$_3$): δ=0.87 (3H, t), 1.27 (6H, m), 1.55 (2H, m), 2.77 (1H, m), 2.90 (2H, m), 3.83 (3H, s), 3.85 (3H, s), 6.78 (2H, m), 6.96 (1H, m).

Example 1

Preparation of N-(2, 6-diisopropylphenyl)-3-(2, 3-methylenedioxyphenyl)octanamide (Compound No. 3 in Table 1)

To a solution of 2.64 g (10 mmol) of 3-(2, 3-methylenedioxyphenyl)octanoic acid in 25 ml of methylene chloride were added 1.46 ml (20 mmol) of thionyl chloride and 0.1 ml of N, N-dimethylformamide, and the resultant mixture was stirred at room temperature for 4 hours and concentrated in vacuo to give 3-(2, 3-methylenedioxyphenyl)octanoic acid chloride as a crude oil. A solution of this acid chloride in 15 ml of methylene chloride was dropwise added to a solution of 1.95 g (11 mmol) of 2, 6-diisopropylaniline and 1.67 ml (12 mmol) of triethylamine in 40 ml of methylene chloride chilled with water under stirring. Stirring was continued for 2 hours, and the reaction mixture was washed with water, dried over anhydrous magnesium sulfate, and the solvent was evaporated. The residue was chromatographed on a silica gel column, eluting with ethyl acetate/hexane (1/6) and crystallized from hexane to give 3.60 g (Yield, 85%) of N-(2, 6-diisopropylphenyl)-3-(2, 3-methylenedioxyphenyl)octanamide as white crystals,
mp. 114°–115° C.

$^1$H NMR (CDCl$_3$): δ=0.85 (t, 3H), 1.0–1.2 (m, 12H), 1.20–1.32 (m, 6H), 1.57–1.74 (m, 2H), 2.50–2.92 (m, 4H), 3.22–3.40 (m, 1H), 5.94 (d, 2H), 6.54 (s, 1H), 6.72–6.84 (m, 3H), 7.07–7.26 (m, 4H).

Examples 2–12

Using the carboxylic acids obtained Reference Examples 2–7 in place of 3-(2, 3-methylenedioxyphenyl) octanoic acid in Example 1, the following compounds were prepared in the same manner as in Example 1.

Example 2

N-(2, 6-Diisopropylphenyl)-3-(2, 3-dimethoxyphenyl)octanamide (Compound No. 29 in Table 1)

mp. 102°–103° C.

$^1$H NMR (CDCl$_3$): δ=0.84 (3H, t), 1.02 (12H, m), 1.25 (6H, m), 1.68 (2H, m), 2.59 (2H, m), 2.78 (2H, m), 3.63 (1H, m), 3.85 (6H, s), 6.82 (3H, m), 7.07 (3H, m), 7.22 (1H, m).

Example 3

N-(2, 6-Diisopropylphenyl)-3-(2, 3-dimethoxyphenyl) heptanamide (Compound No. 28 in Table 1)

mp. 89°–91° C.

$^1$H NMR (CDCl$_3$): δ=0.85 (t, 3H), 1.00–1.10 (m, 12H), 1.12–1.36 (m, 4H), 1.64–1.75 (m, 2H), 2.55–2.65 (m, 2H), 2.79 (d, 2H), 3.57–3.71 (m, 1H), 3.85 (s, 3H), 3.86 (s, 3H), 6.79–6.90 (m, 3H), 7.04–7.11 (m, 3H), 7.19–7.25 (m, 1H).

Example 4

N-(2, 6-Diisopropylphenyl)-3-(2, 3-dimethoxyphenyl) nonanamide (Compound No. 38 in Table 1)

mp. 101°–102° C.

$^1$H NMR (CDCl$_3$): δ=0.85 (t, 3H), 1.03 (t, 12H), 1.07–1.33 (m, 8H), 1.57–1.73 (m, 2H), 2.55–2.71 (m, 2H), 2.79 (d, 2H), 3.56–3.70 (m, 1H), 3.84 (s, 3H), 3.85 (s, 3H), 6.79–6.95 (m, 3H), 7.04–7.10 (m, 3H), 7.14–7.25 (m, 1H).

Example 5

N-(2, 6-Diisopropylphenyl)-2-(2, 3-methylenedioxyphenyl)heptanamide (Compound No. 46 in Table 2)

mp. 142°–143° C.

$^1$H NMR (CDCl$_3$): δ=0.89 (t, 3H), 1.06 (t, 12H), 1.28–1.43 (m, 6H), 1.86–1.98 (m, 1H), 2.24–2.33 (m, 1H), 2.79–2.88 (m, 2H), 3.79 (t, 1H), 5.98–6.00 (m, 2H), 6.72–7.27 (m, 7H).

Example 6

(R)-N-(2, 6-Diisopropylphenyl)-3-(2, 3-methylenedioxyphenyl) octanamide (R-form of compound No. 3 in Table 1)

mp. 127°–128° C.

$^1$H NMR (CDCl$_3$): same as in the racemic N-(2, 6-diisopropylphenyl)-3-(2, 3-methylenedioxyphenyl) octanamide obtained in Example 1.

This compound showed a peak at 17 minutes by HPLC equipped with optically active column (Column: ULTRON ES-OVM (Shinwa Kako Company), Eluent: Methanol-Water (43.5:56.5), Flow: 0.7 ml/min, Detection: UV 270 nm).

Example 7

(S)-N-(2, 6-Diisopropylphenyl)-3-(2, 3-methylenedioxyphenyl) octanamide (S-form of Compound No. 3 in Table 1)

mp. 126°–127° C. $^1$H NMR (CDCl$_3$): same as in racemic N-(2, 6-diisopropylphenyl)-3-(2, 3-methylenedioxyphenyl) octanamide.

This compound showed a peak at 33 minutes by HPLC equipped with optically active column (conditions: same as in Example 6).

Example 8

N-(2, 6-Diisopropylphenyl)-4-(2, 3-methylenedioxyphenyl)nonanamide (Compound No. 65 in Table 2)

mp. 123° C.

$^1$H NMR (CDCl$_3$): δ=0.84 (t, 3H), 1.02–1.26 (m, 18H), 1.40–2.30 (m, 6H), 2.78–2.84 (m, 1H), 2.98–3.10 (m, 2H), 5.91–5.94 (m, 2H), 6.44–6.85 (m, 4H), 7.11–7.32 (m, 3H).

Example 9

N-(2, 6-Diisopropylphenyl)-4-(2, 3-dimethoxyphenyl) nonanamide (Compound No. 84 in Table 3)

mp. 99°–100° C.

$^1$H NMR (CDCl$_3$): δ=0.85 (t, 3H), 1.02–1.27 (m, 18H), 1.63–2.20 (m, 6H), 3.00–3.11 (m, 2H), 3.11–3.30 (m, 1H), 3.80 (s, 3H), 3.88 (s, 3H), 6.78–6.89 (m, 3H), 7.05–7.28 (m, 4H).

Example 10

N-(2, 6-Diisopropylphenyl)-3-(5-acetyl-2, 3-dimethoxyphenyl) octanamide (Compound No. 30 in Table 1)

mp. 99°–101° C.

$^1$H NMR (CDCl$_3$): δ=0.84 (3H, t), 1.00 (12H, m), 1.25 (6H, m), 1.69 (2H, m), 2.58 (2H, m), 2.59 (3H, s), 2.83 (2H, m), 3.74 (1H, m), 3.92 (6H, s), 6.75 (1H, s), 7.07 (2H, m), 7.21 (1H, m), 7.44 (1H, d, J=1.9Hz), 7.52 (1H, d, J=1.9Hz).

Example 11

N-(2, 6-Diisopropylphenyl)-2-(2, 3-dimethoxybenzyl) heptanamide (Compound No. 68 in Table 3)

mp. 128°–130.5° C.

$^1$H NMR (CDCl$_3$): δ=0.90(3H, t), 1.07 (12H, m), 1.3–1.6 (7H, m), 1.84 (1H, m), 2.7–3.1 (5H, m), 3.87 (6H, s), 6.62 (1H; s), 6.8–7.3 (6H, m).

Example 12

(S)-N-(2, 6-Diisopropylphenyl)-3-(2, 3-dimethoxyphenyl)octanamide (S-form of Compound 29 in Table 1)

mp. 100°–101° C.

$^1$H NMR (CDCl$_3$): same as in the racemic compound in Example 2.

This compound showed a peak at 18.4 minutes by HPLC equipped with optical active column (conditions: same as in Example 6). Under said conditions, the racemic compound in Example 2 showed two peaks at 11.3 and 18.4 minutes with same intensity.

Example 13

Preparation of (R)-N-(2, 4, 6-trifluorophenyl)-3-(2, 3-methylenedioxyphenyl) octanamide (R-form of Compound No. 114 in Table 5)

In the same manner as in Example 1, 0.86 g (3.25 mmol) of (R)-3-(2, 3-methylenedioxyphenyl) octanoic acid was converted into its acid chloride. This acid chloride was dissolved in 5 ml of methylene chloride and added dropwise to a solution of 571 mg (3.88 mmol) of 2, 4, 6-trifluoroaniline and 0.54 ml (3.9 mmol) of triethylamine in 15 ml of methylene chloride. The reaction mixture was stirred overnight, washed with water, dried over anhydrous magnesium sulfate and the solvent evaporated. The residue was chromatographed on a silica gel column, eluting with ethyl acetate/hexane (1/5) and recrystallized from a mixed solvent of hexane and a trace of ethyl acetate to give 1.11 g of (R)-N-(2, 4, 6-trifluorophenyl)-3-(2, 3-methylenedioxyphenyl) octanamide as white crystals. Yield, 87%.

mp. 88°–89° C.

$^1$H NMR (CDCl$_3$): δ=0.84 (t, 3H), 1.15–1.30 (m, 6H), 1.70–1.73 (m, 2H), 2.70–2.80 (m, 2H), 3.21–3.33 (m, 1H), 5.92–9.95 (m, 2H), 6.61–6.82 (m, 6H).

Example 14

(R)-N-(2, 4, 6-Trimethoxyphenyl)-3-(2, 3-methylenedioxyphenyl) octanamide (R-form of Compound No. 111 in Table 5)

Using 2, 4, 6-trimethoxyaniline in place of 2, 4, 6-trifluoroaniline in Example 12, the titled compound was prepared as an oil in the same manner as in Example 12.

$^1$H NMR (CDCl$_3$): δ=0.83 (t, 3H), 1.20–1.30 (m, 6H), 1.65–1.80 (m, 2H), 2.66–2.78 (m, 2H), 3.21–3.33 (m, 1H), 3.71 (s, 6H), 3.78 (s, 3H), 5.91–5.94 (m, 2H), 6.10 (s, 2H), 6.44 (s, 1H), 6.70–6.77 (m, 3H).

Reference Example 8

Preparation of 2, 6-diisopropylbenzylamine

To a solution of 7.09 g (40 mmol) of 2, 6-diisopropylaniline in 54 ml of water and 18 ml of conc. hydrochloric acid was dropwise added a solution of 2.76 g (40 mmol) of sodium nitrite in 16 ml of water with sufficient stirring and ice cooling, and the resultant mixture was stirred for further 10 minutes. A solution of 6.64 g (40 mmol) of potassium iodide in 6 ml of water was added to the mixture, and the mixture was stirred for 4 hours at room temperature and refluxed with heating for 1 hour. After cooling, the reaction mixture was extracted with hexane, and the extract was washed with aqueous sodium nitrite and saturated saline in this order, dried over anhydrous magnesium sulfate and the solvent evaporated. The residue was chromatographed on a silica gel column, eluting with hexane to give 5.09 g of 2, 6-diisopropylphenyl iodide as an oil.

To a solution of 5.09 g (17.7 mmol) of 2, 6-diisopropylphenyl iodide in 70 ml of dry ethyl ether was dropwise added 1.6M solution of n-butyllithium in hexane (11.1 ml, 17.8 mmol) at −20° C. The reaction mixture was allowed to warm at 0° C., stirred for 1 hour and poured onto about 100 g of pulverized dry ice. The mixture was allowed to warm gradually to room temperature, mixed with 50 ml of water and the aqueous layer was made alkaline with aqueous sodium hydroxide. The organic layer was separated, and the aqueous layer was washed with ethyl ether, acidified With conc. hydrochloric acid and extracted with ethyl ether. The extract was washed with saturated saline, dried over anhydrous magnesium sulfate, and the solvent evaporated to give 2.53 g of 2, 6-diisopropylbenzoic acid as white solid.

To a suspension of 1.35 g (35.6 mmol) of lithium aluminum hydride in 60 ml of dry tetrahydrofuran was added 3.71 g (18 mmol) of 2, 6-diisopropylbenzoic acid, and the resultant mixture was refluxed with heating for 16 hours. After cooling, 80 ml of water was portionwise added to the mixture, which was mixed with 90 ml of ethyl ether. The mixture was strongly acidified with conc. hydrochloric acid. The aqueous layer was separated and shaken with ethyl ether. The organic layers were combined, washed with aqueous sodium hydroxide and then saturated saline, dried over anhydrous magnesium sulfate, and the solvent was evaporated in vacuo to give 1.37 g of 2, 6-diisopropylbenzyl alcohol as white solid.

To a solution of 1.37 g (7.12 mmol) of 2, 6-diisopropylbenzyl alcohol in 20 ml of toluene was added 0.78 ml (10.7 mmol) of thionyl chloride, and the resultant mixture was stirred at room temperature for 3.5 hours. The reaction mixture was washed with water, dried over anhydrous magnesium sulfate and the solvent evaporated in vacuo to give 1.49 g of 2, 6-diisopropylbenzyl chloride as an oil.

A mixture of 0.92 g (4.4 mmol) of 2, 6-diisopropylbenzyl chloride, 0.97 g (5.24 mmol) of potassium phthalimide and 8 ml of N, N-dimethylformamide was stirred at 70° C. for 1.5 hours. After cooling, the reaction mixture was mixed with water and extracted with ethyl acetate. The extract was washed with saturated saline, dried over anhydrous magnesium sulfate and the solvent evaporated in vacuo. The residue was mixed with 15 ml of hexane and 2 ml of ethyl acetate, stirred at room temperature, and the precipitated crystals were filtered to give 1.01 g of N-(2, 6-diisopropylbenzyl)-phthalimide.

Then, a mixture of 1.01 g (3.14 mmol) of N-(2, 6-diisopropylbenzyl) phthalimide, 0.3 ml of hydrazine hydrate and 15 ml of methanol was refluxed with heating for 3.5 hours. The reaction mixture was concentrated in vacuo, mixed with 20 ml of water and 40 ml of methylene chloride, and made alkaline with aqueous sodium hydroxide. The organic layer was separated, washed with dilute aqueous sodium hydroxide and water, dried over anhydrous magnesium sulfate and the solvent evaporated in vacuo to give 0.53 g of 2, 6-diisopropylbenzylamine as an oil.

$^1$H NMR (CDCl$_3$): δ=1.27 (d, 12H), 1.37 (broad S, 2H), 3.20–3.37 (m, 2H), 3.93 (s, 2H), 7.14–7.27 (m, 3H).

Example 15

Preparation of (R)-N-(2, 6-diisopropylbenzyl)-3-(2, 3-methylenedioxyphenyl) octanamide (R-form of Compound No. 59 in Table 2)

To a solution of 407 mg (1.54 mmol) of (R)-3-(2, 3-methylenedioxyphenyl) octanoic acid in 8 ml of THF were added 0.24 ml of triethylamine and then 0.15 ml (1.6 mmol) of ethyl chloroformate. After stirring for 20 minutes, a solution of 264 mg (1.38 mmol) of 2, 6-diisopropylbenzylamine in tetrahydrofuran was added to the mixture, which was stirred at room temperature for 2 hours. The reaction mixture was mixed with 10 ml of water and shaken with ethyl acetate. The extract was washed with saturated saline, dried over anhydrous magnesium sulfate and the solvent evaporated in vacuo. The residue was recrystallized from a mixed solvent of hexane and ethyl acetate to give 348 mg of (R)-N-(2, 6-diisopropylbenzyl)-3-(2,3-methylenedioxyphenyl) octanamide as white crystals. Yield, 52%.

mp. 133°–134° C.

$^1$H NMR (CDCl$_3$): δ=0.83(t, 3H), 1.15–1.26 (m, 18H), 1.60–1.70 (m, 2H), 2.48–2.52 (m, 2H), 2.90–3.06 (m, 2H), 3.12–3.21 (m, 1H), 4.31 (dd, 1H), 4.50 (dd, 1H), 5.23 (broad S, 1H), 5.64 (d, 1H), 5.78 (d, 1H), 6.62–6.78 (m, 3H), 7.14–7.32(m,3H).

Example 16

Preparation of N-(2, 6-diisopropylbenzyl)-2-(2, 3-methylenedioxyphenyl) heptanamide (Compound No. 58 in Table 2)

Using (R)-2-(2, 3-methylenedioxyphenyl) heptanoic acid in place of (R)-3-(2, 3-methylenedioxyphenyl) octanoic acid in Example 14, N-(2, 6-diisopropylbenzyl)-2-(2, 3-methylenedioxyphenyl) heptanamide was prepared in the same manner as in Example 14.

mp. 134°–135° C.

$^1$H NMR (CDCl$_3$): δ=0.88 (t, 3H), 1.11–1.35 (m, 18H), 1.74–1.83 (m, 1H), 2.12–2.20 (m, 1H), 3.02–3.12 (m, 2H), 3.46 (t, 1H), 4.42 (dd, 1H), 4.52 (dd, 1H), 5.49 (broad S, 1H), 5.73–5.76 (m, 2H), 6.68–6.86 (m, 3H), 7.12–7.31 (m, 3H).

Reference Example 9

Preparation of 3-(2, 3-dimethoxy-5-nitrophenyl) octanoic acid

A mixture of 1.13 g (3.66 mmol) of 3-(2, 3-dimethoxyphenyl) octanoic acid ethyl ester and 3 ml of 60% nitric acid was stirred at room temperature for 2 hours. The reaction mixture was mixed with water and extracted with ethyl acetate. The organic layer was washed with saturated saline, dried over anhydrous magnesium sulfate and the solvent evaporated in vacuo. The residue was chromatographed on a silica gel column, eluting with ethyl acetate/hexane (1/5) to give 1.15 g of 3-(2, 3-dimethoxy-5-nitropheyl) octanoic acid ethyl ester as a yellow oil. Yield, 89%. This compound showed a coupling constant of J=2.6 Hz in $^1$H NMR (CDCl$_3$) spectra, suggesting meta-coupling. Further, 0.10 g of 3-(2, 3-dimethoxy-6-nitrophenyl) octanoic acid etheyl ester (yield, 7.7%) was obtained, showing a coupling constant of J=9.1 Hz in $^1$H NMR (CDCl$_3$) spectra.

A mixture of 1.15 g (3.25 mmol) of 3-(2, 3-dimethoxy-5-nitropheyl) octanoic acid ethyl ester obtained above and 0.46 g (698 mmol) of 85% potassium hydroxide was allowed to react in a mixture of 25 ml of ethanol and 10 ml of water at room temperature for 2 hours and at 50° C. for 30 minutes. The ethanol was evaporated in vacuo, and the remained water was acidified with dilute hydrochloric acid and extracted with ethyl acetate. The organic layer was washed with water, dried over anhydrous magnesium sulfate and the solvent evaporated in vacuo to give 1.06 g of the titled 3-(2, 3-dimethoxy-5-nitrophenyl) octanoic acid. Yield, 100%.

Example 17

Preparation of N-(2, 6-diisopropylphenyl)-3-(2, 3-dimethoxy-5-dimethylaminophenyl) octanamide (Compound No. 35 in Table 1)

A mixture of 3-(2, 3-dimethoxy-5-nitropheyl) octanoic acid and 2, 6-diisopropylaniline was allowed to react in a conventional manner to give N-(2, 6-diisopropylphenyl)-3-(2, 3-dimethoxy-5-nitrophenyl) octanamide.

To a solution of 1.17 g (2.41 mmol) of the amide obtained above in 40 ml of ethanol was added 5% palladium carbon (200 mg), and the resultant mixture was hydrogenated at 50° C. for 4 hours. The catalyst was filtered off, and the filtrated was mixed with 22% hydrogen chloride-ethyl acetate solution (1 ml) and the solvent evaporated in vacuo. To the residue were added 40 ml of ethanol, 37% aqueous formalin (1 ml) and 5% palladium-carbon (300 mg), and the resultant mixture was hydrogenated at 50° C. for 4 hours. The catalyst was filtered off, and the filtrate was concentrated to remove the ethanol. Ethyl acetate and saturated aqueous sodium hydrogencarbonate were added to the residue, and the organic layer was separated, dried over anhydrous magnesium sulfate and the solvent evaporated in vacuo. The residue was chromatographed on a column of silica gel, eluting with ethyl acetate/hexane (1/3) to give 620 mg of N-(2, 6-diisopropylphenyl)-3-(2, 3-dimethoxy-5-diethylamine-phenyl) octanamide as white crystals. Yield, 53%.

mp. 121°–123° C.

$^1$H NMR (CDCl$_3$): δ=0.88(3H, t), 1.04 (12H, m), 1.28 (6H, m), 1.68 (2H, m), 2.65 (2H, m), 2.81 (2H, m), 2.93 (6H, s), 3.52 (1H, m), 3.78 (3H, s), 3.84 (3H, s), 6.16 (1H, d, J=2.6Hz), 6.22 (1H, d, J=2.6Hz), 7.02 (1H, s), 7.1–7.3 (3H, m).

Reference Example 10

Preparation of 2, 6-diisopropyl-3-dimethylaminoaniline 2, 6-Diisopropylformanilide was nitrated with 98% sulfuric acid and 60% nitric acid to give 2, 6-diisopropyl-3-nitroformanilide. This compound was subjected to reduction of nitro group in a conventional manner to give 3-amino-2 6-diisopropylformanilide. This compound was then hydrogenated in the presence of formalin over palladium catalyst to give 2, 6-diisopropyl-3-dimethylaminoformanilide. This compound was heated with conc. hydrochloric acid in ethanol and neutralized with 25% aqueous sodium hydroxide to give 2, 6-diisopropyl-3-dimethylaminoaniline.

Reference Example 11

Preparation of 2, 6-diisopropyl-4-dimethylaminoaniline

To 8.7 g of N-(2, 6-diisopropylphenyl)-p-toluenesulfonamide (8.7 g) were added 6.3 ml of 60% nitric acid, 50 ml of water and 50 ml of acetic acid, then 0.18 g of sodium nitrite, and the resultant mixture was stirred under refluxing and heating for 5 hours. After cooling, the reaction mixture was mixed with 200 ml of water, and the precipitated crystals were filtered and recrystallized from 50 ml of ethanol to give 4.7 g of N-(2, 6-diisopropyl-4-nitropheyl)-p-toluenesulfonamide. This compound was hydrolyzed in aqueous sulfuric acid to give 2.7 g of 2, 6-diisopropyl-4-nitroaniline.

Then, 2, 6-diisopropyl-4-nitroaniline was converted into 2, 6-diisopropyl-4-nitroformanilide in a conventional manner and the latter was hydrogenated over palladium catalyst in the presence of formalin to give 2, 6-diisopropyl-4-dimethylaminoformanilide. This compound was heated with conc. hydrochloric acid in ethanol and neutralized with 25% aqueous sodium hydroxide to give 2, 6-diisopropyl-4-dimethylaminoaniline.

Example 18

Preparation of (R)-N-(2, 6-diisopropyl-3-dimethylaminophenyl)-3-(2, 3-methylenedioxyphenyl) octanamide hydrochloride (hydrochloride of Compound No. 102 in Table 5)

To a solution of 1.3 g (4.9 mmol) of (R)-3-(2, 3-methylenedioxyphenyl) octanoic acid in 20 ml of methylene chloride were added 1.1 ml of thionyl chloride and 0.1 ml of N, N-dimethylformamide, and the resultant mixture was refluxed under stirring for 2 hours. The reaction mixture was concentrated in vacuo to give (R)-3-(2, 3-methylenedioxyphenyl) octanoyl chloride as an oil. This oil was dissolved in methylene chloride to give a solution, which was dropwise added to a solution of 1.08 g (4.9 mmol) of 2, 6-diisopropyl-3-dimethylaniline and 1.0 ml of triethylamine in 20 ml of methylene chloride (5°–10° C.). The reaction mixture was allowed to react at room temperature overnight and chromatographed on a silica gel column, eluting with ethyl acetate/hexane to give 1.16 g of gelatinous material. This was dissolved in acetone and mixed with 22% solution of hydrogen chloride in 2 ml of ethyl acetate. The resultant mixture (hydrochloride) was concentrated and crystallized from hexane to give 1.23 g of (R)-N-(2, 6-diisopropyl-3-dimethylaminophenyl)-3-(2, 3-methylenedioxyphenyl) octanamide hydrochloride. Yield, 50%.

mp. 114°–116° C.

$^1$H NMR (CDCl$_3$): $\delta$ = 0.86 (t, 3H), 0.99 (m, 6H), 1.26 (d, 12H), 1.70 (m, 2H), 2.73–3.34 (m, 10H), 3.82 (broad S, 1H), 5.93 (d, 2H), 6.70–6.80 (m,3H), 7.01 (broad S, 1H), 7.24 (broad S, 2H).

Example 19

Preparation of (R)-N-(2, 6-diisopropyl-4-dimethylaminophenyl)-3-(2, 3-methylenedioxyphenyl) octanamide hydrochloride (Hydrochloride of Compound No. 105 in Table 5)

Using 2, 6-diisopropyl-4-dimethylaminoaniline in place of 2, 6-diisopropyl-3-dimethylaminoaniline in Example 17, the reaction was effected in the same manner as in Example 17 to give (R)-N-(2, 6-diisopropyl-4-dimethylaminophenyl)-3-(2, 3-methylenedioxyphenyl) octanamide hydrochloride.

mp. 158°–160° C.

$^1$H NMR (CDCl$_3$): $\delta$ = 0.85 (t, 3H), 1.03 (d, 12H), 1.14 (m, 6H), 1.69 (m, 2H), 2.73–2.96 (m, 4H), 3.05 (s, 6H), 3.32 (m, 1H), 5.94 (dd, 2H), 6.72–6.83 (m, 3H), 6.89 (broad S, 1H), 7.27 (broad S, 2H).

Reference Example 12

Preparation of (R)-2-(2, 3-methylenedioxyphenyl) heptanoic acid

A salt obtained from ($\pm$)-2-(2, 3-methylenedioxyphenyl)heptanoic acid and (S)-1-phenylethylamine was recrystallized three times from a mixed solvent of ethyl acetate-heptane (1:9). The salt was mixed with hydrochloric acid and extracted with methylene chloride. The organic layer was washed with dilute hydrochloric acid, dried over anhydrous magnesium sulfate and the solvent evaporated to give (R)-2(2, 3-methylenedioxyphenyl)heptanoic acid. Yield, 39%.

mp. 47°–48° C. $[\alpha]_D^{25} - 64.5°$ C. (MeOH, c = 1.01).

Reference Example 13

Preparation of (R)-2-(2, 3-methylenedioxyphenyl) heptylamine

To a solution of 97.45 g (0.389 mmol) of (R)-2-(2, 3-methylenedioxyphenyl) heptanoic acid in 390 ml of methylene chloride were added 56.8 ml of thionyl chloride and 0.9 ml of N, N-dimethylformamide, and the resultant mixture was stirred at room temperature for 3 hours and concentrated in vacuo to give its acid chloride. This was dissolved in 390 ml of methylene chloride and dropwise added into a mixture of 117 ml of conc. aqueous ammonia and 230 ml of methylene chloride with ice cooling and stirring. The reaction mixture was stirred at room temperature for 1 hour, mixed with water and the aqueous layer was separated. The organic layer was washed with water, dried over anhydrous magnesium sulfate and the solvent evaporated in vacuo to give 96.9 g of (R)-2-(2, 3-methylenedioxyphenyl) heptanamide.

To a mixture, warmed at about 70° C., of 18.92 g of sodium borohydride (NaBH$_4$) and 250 ml of dioxane was dropwise added a solution of 24.93 g (0.1 mol) of R-2-(2, 3-methylenedioxyphenyl) heptanamide and 28.6 ml of acetic acid in 125 ml of dioxane. The resultant mixture was refluxed under heating for 3 hours, allowed to cool and added portionwise to an ice-cooled solution of 75 ml of. conc. hydrochloric acid and 250 ml of water. The reaction mixture was heated at about 60° C. for 1 hours, allowed to cool, washed with hexane, made alkaline with aqueous sodium hydroxide and shaken with heptane. The extract was washed with saturated saline, dried over anhydrous sodium sulfate, the solvent evaporated in vacuo to give 21.6 g of (R)-2-(2, 3-methylenedioxyphenyl) heptylamine as an oil.

¹H NMR (CDCl₃): δ=0.84 (t, 3H), 1.0–1.4 (m, 8H), 1.57–1.66 (m, 2H), 2.70–2.93 (m, 3H), 5.92 (s, 2H), 6.64–6.83 (m, 3H).

Reference Example 14

Preparation of 1-amino-2-(1-methylethoxy)-5, 6, 7, 8-tetrahydronaphthalene (i) Preparation of 1-nitro-5, 6, 7, 8-tetrahydro-2-naphthol:

To a solution of 25.9 g of 5, 6, 7, 8-tetrahydronaphthol in 210 ml of ether was dropwise added 60% nitric acid at 15°–20° C. with stirring in 1 hour, and the resultant mixture was stirred at room temperature for 3 hours. The reaction mixture was washed with water (6 times) and saturated saline and the organic layer was dried over anhydrous sodium sulfate and concentrated in vacuo. The residue was chromatographed on a column of silica gel, eluting with ethyl acetate/n-hexane (1:15) to give 10.12 g of 1-nitro-5, 6, 7, 8-tetrahydro-2-naphthol.

(ii) Preparation of 2-(1-methylethoxy)-1-nitro-5, 6, 7, 8-tetrahydronaphthalene:

A mixture of 4.83 g of 1-nitro-5, 6, 7, 8-tetrahydro-2-naphthol obtained in (i), 5.95 g of isopropyl iodide, 5.18 g of potassium carbonate, 0.40 g of cupric oxide (II) and 30 ml of N, N-dimethylformamide was stirred at 100° C. for 1.5 hours. The reaction mixture was allowed to cool to room temperature, mixed with ethyl acetate and filtered through Celite to remove the insoluble part. The filtrate was concentrated in vacuo, and the residue was mixed with water. The precipitated crystals were filtered to give 5.18 g of 2-(1-methylethoxy)-1-nitro-5, 6, 7, 8-tetrahydronaphthalene.

(iii) A mixture of 5 g of iron dust, 0.5 g of acetic acid and 3.5 ml of water was refluxed under heating for 30 minutes, allowed to cool at 80° C., mixed with 14 ml of 2-propanol and gradually mixed with 5.00 g of 2-(1-methylethoxy)-1-nitro-5, 6, 7, 8-tetrahydronaphthalene obtained in (ii). The reaction mixture was stirred at the same temperature for 1 hour, allowed to cool by 40° C., mixed with a solution of 1.5 g of potassium carbonate in 2.5 ml of water and stirred further for 1 hour. Acetone was added to the mixture, which was filtered through Celite. The filtrate was concentrated in vacuo, and the residue was mixed with water and extracted with ether. The organic layer was washed with water and saturated saline, dried over anhydrous sodium sulfate and concentrated in vacuo to give 4.26 g of the titled compound.

¹H-NMR (CDCl₃-TMS): δ=1.34 (6H,d), 1.77 (4H, m), 2.44 (2H, t), 2.6–2.72 (4H, m), 4.4 (1H, obs. quint), 6.45, 6.65 (each 1H, d).

The following compounds were prepared in the same manner as above.

1-Amino-2-methoxy-5, 6, 7, 8-tetrahydronaphthalene:

¹H-NMR (CDCl₃-TMS): δ=1.73, 1.85 (each 2H, m), 2.49, 2.70 (each 2H, obs. t), 3.65 (2H, br.s), 3.83 (3H, s), 6.51, 6.65 (each 1H ,d).

1-Amino-2-ethoxy-5, 6, 7, 8-tetrahydronaphthalene:

¹H-NMR(CDCl₃-TMS): δ=1.41 (3H, t), 1.73, 1.84 (each 2H, m), 2.48, 2.69 (each 2H, obs.t), 3.65 (2H, br.s), 4.04 (2H, q), 6.48, 6.63 (each 1H, d).

Reference Example 15

Preparation of 4-amino-5-ethoxyindane (i) Preparation of 5-ethoxy-4-nitroindane:

To a solution of 13.4 g of 5-hydroxyindane in 130 ml of ether was dropwise added 60% nitric acid at 15°–20° C. with stirring in 45 minutes, and the resultant mixture was stirred at room temperature for 2 hours. The reaction mixture was washed with water (6 times) and saturated saline. The organic layer was dried over anhydrous sodium sulfate and concentrated in vacuo. The residue was chromatographed on a silica gel column, eluting with ethyl acetate-n-hexane (1:15) to give 15.34 g of a mixture of 5-hydroxy-4-nitroindane and 5-hydroxy-6-nitroindane.

A mixture of 15.3 g of a mixture of 5-hydroxy-4-nitroindane and 5-hydroxy-6-nitroindane obtained above, 20.0 g of ethyl iodide, 17.7 g of potassium carbonate, 1.36 g of cupric oxide (II) and 100 ml of N, N-dimethylformamide was stirred at 100° C. for 1.5 hours. After finishing the reaction, the solvent was evaporated in vacuo, and the residue was mixed with water and shaken with ethyl acetate. The organic layer was washed with water (twice) and saturated saline in order, dried over anhydrous sodium sulfate and the solvent evaporated. The residue was chromatographed on a silica gel column, eluting with toluene-n-hexane (1:3) to give 6.12 g of 5-ethoxy-4-nitroindane.

(ii) A solution of 6.04 g of 5-ethoxy-4-nitroindane obtained in (i) in 60 ml of ethanol was hydrogenated over 5% palladium/C to give 4.92 g of the titled compound.

¹H-NMR(CDCl₃-TMS): δ=1.41 (3H, t), 2.10 (2H, quint), 2.73, 2.85 (each 2H, t), 3.70 (2H, br.s), 4.03 (2H, q), 6.60, 6.64 (each 1H, d).

Example 20

Preparation of (R)-1-[2-(2, 3-methylenedioxyphenyl) heptyl]-3-(2-isopropoxy-5, 6, 7, 8-tetrahydronaphthalene-1-yl) urea (Compound No. 169 in Table 8)

To a solution of 20.0 g (0.0974 mol) of 1-amino-2-isoproxy-5, 6, 7, 8-tetrahydronaphthalene in 400 ml of methylene chloride were dropwise added 12.1 g (0.0408 mol) of bis (trichloromethyl) carbonate (namely triphosgene) and 23.4 g (0.233 mol) of triethylamine, and the resultant mixture was refluxed with heating for 1.5 hours. After cooling by room temperature, the reaction mixture was mixed with 22.9 g (0.0973 mol) of (R)-2-(2, 3-methylenedioxyphenyl) heptylamine and allowed to react at room temperature overnight. To the reaction mixture were added a small amount of aqueous ammonia and water, and the aqueous layer was extracted with methylene chloride. The organic layers were combined, washed with water, dried over anhydrous magnesium sulfate and the solvent evaporated. The residue was chromatographed on a silica gel column, eluting with hexane-ethyl acetate (1:5) and recrystallized from a mixed solvent of heptane and ethyl acetate to give 34.81 g of the titled compound.

mp. 115° C.

¹H-NMR(CDCl₃-TMS): δ=0.83 (3H, t), 1.22 (6H, m), 1.25 (6H, d), 1.61–1.65 (6H, m), 2.49, 2.67 (each 2H, m), 2.88 (1H, m), 3.32 (1H, m), 3.55 (1H, m), 4.37 (1H, obs. quint), 4.45 (1H, t), 5.52 (1H, s), 5.72, 5.74 (each 1H, s), 6.56 (1H, dd), 6.63–6.73 (3H, m), 6.94 (1H, d).

Example 21

Preparation of (R)-1-[2-(2, 3-methylenedioxyphenyl) heptyl]-3-(2-methoxy-5, 6, 7, 8-tetrahydronaphthalene-1-yl) urea (Compound No. 183 in Table 8)

Using 1-amino-2-methoxy-5, 6, 7, 8-tetrahydronaphthalene in place of 1-amino-2-(1-methylethoxy)-5, 6, 7, 8-tetrahydronaphthalene in Example 20,-the reaction was effected in the same manner as in Example 20 to give the titled compound.

mp. 137°–138° C.

$^1$H-NMR(CDCl$_3$-TMS): δ=0.83 (3H, t), 1.22 (6H, m), 1.58–1.66 (6H, m), 2.50, 2.67 (each 2H, m), 2.89 (1H, m), 3.30 (1H, m), 3.55 (1H, m), 3.70 (3H, s), 4.42 (1H, t), 5.60 (1H, s), 5.74, 5.74 (each 1H, s), 6.57 (1H, dd), 6.65–6.74 (3H, m), 6.96 (1H, d).

Example 22

Preparation of (R)-1-[2-(2, 3-methylenedioxyphenyl) heptyl]-3-(2-ethoxy-5, 6, 7, 8-tetrahydronaphthalene-1-yl) urea (Compound No. 184 in Table 8)

Using 1-amino-2-ethoxy-5, 6, 7, 8-tetrahydronaphthalene in place of 1-amino-2-(1-methylethoxy)-5, 6, 7, 8-tetrahydronaphthalene in Example 20, the reaction was effected in the same manner as in Example 20 to give the titled compound.

mp. 81.5°–82.5° C.

$^1$H-NMR(CDCl$_3$-TMS): δ=0.83 (3H, t), 1.22 (6H, m), 1.32 (3H, t), 1.60–1.65 (6H, m), 2.50, 2.67 (each 2H, m), 2.88 (1H, m), 3.32 (1H, m), 3.55 (1H, m), 3.91 (2H, q), 4.45 (1H, t), 5.52 (1H, s), 5.71, 5.74 (each 1H, s), 6.57 (1H, dd), 6.65–6.73 (3H, m), 6.95 (1H, d).

Example 23

Preparation of (R)-1-[2-(2, 3-methylenedioxyphenyl) heptyl]-3-(5-ethoxyindane-4-yl) urea (Compound No. 185 in Table 8)

Using 4-amino-5-ethoxyindane in place of 1-amino-2-(1-methylethoxy)-5, 6, 7, 8-tetrahydronaphthalene in Example 20, the reaction was effected in the same manner as in Example 20 to give the titled compound.

mp. 108°–109° C.

$^1$H-NMR(CDCl$_3$-TMS): δ=0.83 (3H, t), 1.22 (6H, m), 1.33 (3H, t), 1.63 (2H, m), 1.93 (2H, quint), 2.60 (2H, dt), 2.80 (2H,t), 2.90 (1H,m), 3.30 (1H, m), 3.60 (1H, m), 3.93 (2H, q), 4.55 (1H, t), 5.69, 5.75 (each 1H, s), 5.81 (1H, s), 6.60 (1H, dd), 6.64–6.77 (3H, m), 7.00 (1H, d).

Example 24

Preparation of (R)-1-[2-(2, 3-methylenedioxyphenyl) heptyl]-3-(2, 3-dihydro-2, 2-dimethylbenzofuran-7-yl) urea (Compound No. 186 in Table 8)

A mixture of 0.90 g of 2, 3-dihydro-2, 2-dimethylbenzofuran-7-carboxylic acid, 1.38 g of diphenylphosphoryl azide, 0.61 g of triethylamine and 12 ml of toluene was stirred at 90° C. for 2 hours and allowed to cool with ice. To this mixture was added a solution of 1.18 g of (R)-2-(2, 3-methylenedioxyphenyl) heptylamine in 10 ml of toluene under ice cooling and stirring, and the resultant mixture was stirred at room temperature for 2 hours and mixed with 30 ml of n-hexane. The precipitated crystals were filtered and recrystallized from ethyl acetate to give 1.02 g of the titled compound.

mp. 161°–162° C.

$^1$H-NMR(CDCl$_3$-TMS): δ=0.84 (3H, t), 1.24 (6H, m), 1.44 (6H, s), 1.62 (2H, m), 2.95 (1H, m), 3.00 (2H, s), 3.29 (1H, m), 3.69 (1H, m), 4.73 (1H, t), 5.85, 5.87 (each 1H, s), 6.04 (1H, s), 6.60 (1H, dd), 6.71–6.83 (4H, m), 7.39 (1H,d).

Reference Example 16

Preparation of (R)-2-(2, 3-methylenedioxyphenyl)heptanoic acid

A salt obtianed from (±)-2-(2, 3-methylenedioxyphenyl) heptanoic acid and (S) -1phenylethylamine was three times recrystallized from a mixed solvent of ethyl acetate-heptane (1:9). This salt was treated with hydrochloric acid and extracted with ethylene chloride. The organic layer was washed with dilute hydrochloric acid, dried over anhydrous magnesium sulfate and the solvent evaporated to give (R )-(2, 3-methylenedioxyphenyl) heptanoic acid. Yield, 39%.

mp. 47°–48° C. $[α]_D^{25}$ −64.5° C. (MeOH, c=1.01).

Reference Example 17

Preparation of (R)-2-(2, 3-methylenedioxyphenyl) heptylamine

To a solution of 97.45 g of (0.389 mol) of (R)-2-(2, 3-methylenedioxyphenyl) heptanoic acid in 390 ml of methylene chloride were added 56.8 ml of thionyl chloride and 0.9 ml of N, N-dimethylformamide, and the resultant mixture was stirred at room temperature for 3 hours. The reaction mixture was concentrated in vacuo to give its acid chloride. This was dissolved in 390 ml of methylene chloride to give a solution, which was dropwise added into a mixture of 117 ml of conc. aqueous ammonia and 230 ml of methylene chloride under ice cooling and stirring. The reaction mixture was stirred at room temperature for 1 hours and mixed with water. The organic layer was separated, washed with water, dried over anhydrous magnesium sulfate and the solvent evaporated in vacuo to give 96.9 g of (R)-2-(2, 3-methylenedioxyphenyl) heptanamide.

To a mixture, heated at about 70° C., of 18.92 g of sodium borohydride (NaBH$_4$) and 250 ml of dioxane was dropwise added a solution of 24.93 g (0.1 mol) of (R)-2-(2, 3-methylenedioxyphenyl) heptaneamide and 28.6 ml of acetic acid in 125 ml of dioxane, and the resultant mixture was refluxed with heating for 3 hours. After cooling, the mixture was portionwise added to an ice-cooled solution of 75 ml of conc. hydrochloric acid and 250 ml of water, and the resultant mixture was heated at about 60° C. for 1 hour, washed with hexane, made alkaline with aqueous sodium hydroxide and extracted with heptane. The extract was washed with saturated saline, dried over anhydrous sodium sulfate and the solvent evaporated in vacuo to give 21.6 g of (R)-[2-(2, 3-methylenedioxyphenyl) heptylamine as an oil.

$^1$H NMR (CDCl$_3$): δ=0.84 (t, 3H), 1.0–1.4 (m, 8H), 1.57–1.66 (m, 2H), 2.70–2.93 (m, 3H), 5.92 (s, 2H), 6.64–6.83 (m, 3H).

Reference Example 18

Preparation of 5-amino-4, 6-bis (dimethylamino) pyrimidine (1) Preparation of 4, 6-bis (dimethylamino)-5-nitropyrimidine:

To a mixture of 4.85 g of 4, 6-dichloro-5-nitropyrimidine, 7.59 g of potassium carbonate and 50 ml of acetone was dropwise added 50% aqueous dimethylamine (6.76 g) with water cooling and stirring, and the resultant mixture was stirred at room temperature for 30 minutes. The precipitated salts were filtered off, and the filtrate was concentrated in vacuo. The residue was dissolved in ethyl acetate to give a solution, which was filtered to remove the insoluble part. The filtrate was concentrated, and the residue was mixed with n-hexane and triturated. The precipitated crystals were filtered to give 5.10 g of 4, 6-bis (dimethylamino)-5-nitropyrimidine.

(ii) A mixture of 5 g of iron dust, 0.5 g of acetic acid and 3.5 ml of water was refluxed under heating for 30 minutes, allowed to cool at 80° C. and mixed with 14 ml of 2-propanol and gradually mixed with 4.22 g of 4, 6-bis (dimethylamino)-5-nitropyrimidine. The resultant mixture was stirred at the same temperature for 1 hour, allowed to cool at 40° C., mixed with a solution of 1.5 g of potassium carbonate in 2.5 ml of water and stirred for 1 hour. Acetone was added to the mixture, which was filtered through Celite. The filtrate was concentrated in vacuo, and the residue was mixed with water and shaken with ether. The organic layer was washed with water and saturated saline in order, dried over anhydrous sodium sulfate and the solvent evaporated to give 3.32 g of the titled compound.

The following compounds were prepared in the same manner as above:

$^1$H-NMR (CDCl$_3$-TMS): $\delta$=2.89 (12H, s), 3.38 (2H, br.s), 8.15 (1H, s).

5-Amino-4, 6-dipyrrolidinopyrimidine:

$^1$H-NMR (CDCl$_3$-TMS): $\delta$=1.92 (8H, t), 3.02 (2H, br.s), 3.50 (8H, t), 8.03 (1H, s).

5-Amino-4, 6-dimorpholinopyrimidine.

$^1$H-NMR (CDCl$_3$-TMS): $\delta$=3.29 (8H, t), 3.43 (2H, s), 3.85 (8H, t), 8.20 (1S, s).

Example 25

Preparation of (R)-1-[2-(2, 3-methylenedioxyphenyl) heptyl]-3-[4, 6-bis (dimethylamino) pyrimidine-5-yl]urea (Compound No. 216 in Table 10)

To a solution of 23.78 g (0.1405 mol) of 5-amino-4, 6-bis (dimethylamino) pyrimidine in 476 ml of methylene chloride were added 17.4 g (0.0586 mol) of bis(trichloromethyl) carbonate (namely triphosgene) and 34.1 g (0.337 mol) of triethylamine, and the resultant mixture was refluxed with heating for 1.5 hours. The reaction mixture was allowed to cool at room temperature, mixed with 33.0 g (0.1402 mol) of (R)-2-(2, 3-methylenedioxyphenyl)-heptylamine and allowed to react at room temperature overnight. The reaction mixture was mixed with a small amount of aqueous ammonia and water, and the aqueous layer was extracted with methylene chloride. The organic layer was washed with water, dried over anhydrous magnesium sulfate and the solvent evaporated. The residue was chromatographed on a silica gel column, eluting with chloroform-1% methanol/chloroform-2% methanol/chloroform and recrystallized from heptane and ethyl acetate to give 41.0 g of the titled compound.

mp. 151.0°–151.5° C.

$^1$H-NMR (CDCl$^3$-TMS): $\delta$=0.83 (3H, t), 1.22 (6H, m), 1.56 (2H, m), 2.84 (1H, quint), 3.00 (12H, s), 3.38 (1H, m), 3.43 (1H, m), 4.33 (1H, t), 5.51 (1H, s), 5.82, 5.88 (each 1H, s), 6.52 (1H, dd), 6.68–6.75 (2H, m), 8.10 (1H, s).

Example 26

Preparation of (R)-1-[2-(2, 3-methylenedioxyphenyl) heptyl]-3-(4, 6-dipyrrolidinopyrimidine-5-yl) urea (Compound No. 217 in Table 10)

Using 5-amino-4, 6-dipyrrolidinopyrimidine in place of 5-amino-4, 6-bis (dimethylamino) pyrimidine in Example 25, the reaction was effected in the same manner as in Example 25 to give the titled compound.

mp. 199°–200.5° C.

$^1$H-NMR (CDCl$_3$-TMS): $\delta$=0.83 (3H, t), 1.21 (6H, m), 1.60 (2H, m), 1.80 (8H, m), 2.85 (1H, quint), 3.44 (2H, t), 3.52 (8H, m), 4.49 (1H, t), 5.37 (1H, s), 5.80, 5.87 (each 1H, s), 6.52 (1H, dd), 6.68 (1H, dd), 6.73 (1H, dd), 8.07 (1H, s).

Example 27

Preparation of (R)-1-[2-(2, 3-methylenedioxyphenyl) heptyl]-3-(4, 6-dimorpholinopyrimidine-5-yl) urea (Compound No. 218 in Table 10)

Using 5-amino-4, 6-dimorpholinopyrimidine in place of 5-amino-4, 6-bis (dimethylamino) pyrimidine in Example 25, the reaction was effected in the same manner as in Example 25 to give the titled compound.

mp. 128°–132° C.

$^1$H-NMR (CDCl$_3$-TMS): $\delta$=0.83 (3H, t), 1.21 (6H, m), 1.60 (2H, m), 2.85 (1H, m), 3.20–3.39 (9H, m), 3.63 (1H, m), 3.69 (8H, t), 5.38 (1H, t), 5.42 (1H, s), 5.68, 5.75 (each 1H, s), 6.52 (1H, dd), 6.66–6.75 (2H, m), 8.32 (1H, s).

Reference Example 19

Preparation of 5-amino-4, 6-dimethoxypyrimidine (i) Preparation of 4, 6-dimethoxy-5-nitropyrimidine:

To a suspension of 60% sodium hydride/oil (2.64 g) in 50 ml of methanol was added gradually 5.82 g of 4, 6-dichloro-5-nitropyrimidine under water cooling, and the resultant mixture was stirred at room temperature for 30 minutes and the solvent evaporated in vacuo. The residue was mixed with water, and the precipitated crystals were filtered and washed with water and n-hexane in order to give 5.10 g of 4, 6-dimethoxy-5-nitropyrimidine.

(ii) A mixture of 5 g of iron dust, 0.5 g of acetic acid and 3.5 ml of water was refluxed with heating for 30 minutes, allowed to cool at 80° C. and mixed with 14 ml of 2-propanol and gradually 4.26 g of 4, 6-dimethoxy-5-nitropyrimidine obtained in (i). The resultant mixture was stirred at the same temperature for 1 hour, allowed to cool at 40° C., mixed with a solution of 1.5 g of potassium carbonate in 2.5 ml of water and stirred further for 1 hour. Acetone was added to the mixture, which was filtered through Celite. The filtrate was concentrated in vacuo, and the residue was mixed with water and shaken with ether. The organic layer was washed with saturated saline, dried over anhydrous sodium sulfate and the solvent evaporated to give 3.55 g of the titled compound.

$^1$H-NMR (CDCl$_3$-TMS): $\delta$=3.54 (2H, br. s), 4.01 (6H, s), 7.98 (1H, s) NMR.

Example 28

Preparation of (R)-1-[2-(2, 3-methylenedioxyphenyl) heptyl]-3-(4, 6-dimethoxypyrimidine-5-yl) urea (Compound No. 219 in Table 10)

(i) Preparation of N-phenoxycarbonyl-(R)-2-(2, 3-methylenedioxyphenyl) heptylamine:

To a mixture of 2.35 g of (R)-2-(2, 3-methylenedioxyphenyl) heptylamine, 1.20 g of triethylamine and 20 ml of ethyl acetate was dropwise added 1.72 g of phenyl chloroformate with ice cooling and stirring, and the resultant mixture was stirred at room temperature for 2 hours. The reaction mixture was washed with water and saturated saline in this order, dried over anhydrous sodium sulfate and the solvent evaporated to give 3.51 g of N-phenoxycarbonyl-(R)-2-(2, 3-methylenedioxyphenyl) heptylamine.

$^1$H-NMR (CDCl$_3$-TMS): $\delta$=0.85 (3H, t), 1.26 (6H, m), 1.67 (2H, m), 3.02 (1H, quint), 3.38 (1H, m), 3.63 (1H, m), 4.95 (1H, br. s), 5.94 (2H, s), 6.69, 6.75 (each 1H, d), 6.83 (1H, t), 7.06 (2H, d), 7.16 (1H, t), 7.34 (2H, obs.quint).

(ii) A mixture of 0.78 g of 5-amino-4, 6-dimethoxypyrimidine, 1.78 g of N-phenoxycarbonyl-(R)-2-(2, 3-methylenedioxyphenyl) heptylamine, obtained in (i) 0.76 g of 1, 8-diazabicyclo [5, 4, 0] undec-7-ene and 8 ml of dioxane was refluxed under heating and stirring for 25 hours and the solvent evaporated. The residue was chromatographed on a silica gel column, eluting with chloroform-2-propanol (20:1) and then with ethyl acetate-n-hexane (1:1→2:1) to give 0.15 g of the titled compound.

mp. 196°–197° C.

$^1$H-NMR (CDCl$_3$-TMS): $\delta$=0.83 (3H, t), 1.23 (6H, m), 1.63 (2H, m), 2.93 (1H, m), 3.31 (1H, m), 3.62 (1H, m), 3.91 (6H, s), 4.78 (1H, br.s), 5.48 (1H, s), 5.85 (2H, s), 6.58 (1H, dd), 6.71 (1H, dd), 6.76 (1H, dd), 8.27 (1H, s).

Reference Example 20

Preparation of 5-amino-4, 6-di (1-methylethoxy) pyrimidine (i) Preparation of 4, 6-di (1-methylethoxy)-5-nitropyrimidine:

To a mixture of 6.28 g of 4, 6-dihydroxy-5-nitropyrimidine, 6.00 g of 2-propanol, 10.5 g of triphenylphosphine and 80 ml of tetrahydrofuran was added 6.97 g of diethyl azodicarboxylate at room temperature with stirring, and the resultant mixture was stirred for 2 hours, mixed with 10.5 g of triphenylphosphine and 6.97 g of diethyl azodicarboxylate, stirred for 11 hours, again mixed with 10.5 g of triphenylphosphine and 6.97 g of diethyl azodicarboxylate and stirred for further 11 hours. The precipitate was filtered off, and the filtrate was concentrated in vacuo. The residue was mixed with ether, and the insoluble material was filtered off. The filtrate was concentrated in vacuo, and the residue was chromatographed on a silica gel column, eluting with ethyl acetate-n-hexane (1:14) to give 3.13 g of 4, 6-di (1-methylethoxy)-5-nitropyrimidine.

$^1$H-NMR (CDCl$_3$-TMS): $\delta$=1.37 (12H, d), 5.44 (2H, obs. quint), 8.37 (1H, s).

(ii) A mixture of 3 g of iron dust, 0.3 g of acetic acid and 2.5 ml of water was refluxed with heating for 30 minutes, allowed to cool at 80° C. and mixed with 10 ml of 2-propanol and gradually 3.10 g of 4, 6-di (1-methylethoxy)-5-nitropyrimidine obtained in (i). The resultant mixture was stirred at the same temperature for 1.85 hours, allowed to cool at 40° C. mixed with a solution of 1 00 g of potassium carbonate in 2.5 ml of water and stirred for further 1 hour. Acetone was added to the mixture, which was filtered through Celite. The filtrate was concentrated in vacuo, and the residue was mixed with water and shaken with ether. The organic layer was washed with saturated saline, dried over anhydrous sodium sulfate and the solvent evaporated. The residue was chromatographed on a column of silica gel, eluting with ethyl acetate-n-hexane (1:10) to give 2.37 g of the titled compound.

$^1$H-NMR (CDCl$_3$-TMS): $\delta$=1.36 (12H, d), 3.50 (2H, br. s), 5.33 (2H, obs. quint), 7.94 (1H, s).

Example 29

Preparation of (R)-1-[2-(2, 3-methylenedioxyphenyl) heptyl]-3-[4, 6-di (1-methylethoxy) pyrimidine-5-yl]urea (Compound No. 220 in Table 10)

(i) Preparation of 4, 6-di (1-methylethoxy)-5-ethoxycarbonyl-aminopylimidine:

To a mixture of 0.42 g of 5-amino-4, 6-di (1-methylethoxy) pyrimidine, 0.30 g of pyridine and 8 ml of methylene chloride was dropwise added 0.26 g of ethyl chloroformate at room temperature with stirring, and the resultant mixture was stirred for 5 hours. The reaction mixture was washed with water and saturated saline in order, dried over anhydrous sodium sulfate and the solvent evaporated. The residue was chromatographed on a silica gel column, eluting with ethyl acetate-n-hexane (1:5) to give 0.29 g of 4, 6-di (1-methylethoxy)-5-ethoxycarbonyl-aminopyrimidine.

$^1$H-NMR (CDCl$_3$-TMS): $\delta$=1.29 (3H, t), 1.35 (12H, d), 4.19 (2H, q), 5.35 (2H, obs. quint), 5.70 (1H, br.s), 8.25 (1H, s).

(ii) A mixture of 0.28 g of 4, 6-di (1-methylethoxy)-5-ethoxycarbonylaminopyrimidine obtained in (i), 0.24 g of (R)-2-(2, 3-methylenedioxyphenyl) heptylamine, 0.15 g of 1, 8-diazabicyclo [5, 4, 0] undec -7-ene and 5 ml of toluene was stirred at 110° C. for 10.5 hours, and the solvent was evaporated. The residue was chromatographed on a silica gel column, eluting with ethyl acetate-n-hexane (2:5→1:2) to give 0.27 g of the titled compound.

mp. 96.5°–98° C.

$^1$H-NMR (CDCl$_3$-TMS): $\delta$=0.83 (3H, t), 1.22 (6H, m), 1.28, 1.31 (each 6H, d), 1.63 (2H, m), 2.89 (1H, quint), 3.30 (1H, m), 3.59 (1H, m), 4.87 (1H, t), 5.30 (2H, obs. quint), 5.46 (1H, s), 5.77, 5.81 (each 1H, s), 6.57 (1H, dd), 6.67 (1H, dd), 6.71 (1H, dd), 8.22 (1H, s).

Reference Example 21

Preparation of 5-amino-4-dimethylamino-6-ethoxypyrimidine:

(i) Preparation of 4-chloro-6-dimethylamino-5-nitropyrimidine

To a mixture of 7.76 g of 4, 6-dichloro-5-nitropyrimidine, 3.70 g of sodium hydrogencarbonate and 80 ml of acetone was gradually dropwise added 50% aqueous dimethylamine (3.79 g) with ice cooling and stirring, and the mixture was stirred at room temperature for 30 minutes. Every 30 minutes, 50% aqueous dimethylamine (0.7 g) was added three times to the mixture, and the solvent was evaporated in vacuo. The residue was mixed with 70 ml of ethyl acetate, heated at 45° C. and the insoluble material was filtered off. The filtrate was dried over anhydrous sodium sulfate and the solvent evaporated. The residue was mixed with n-hexane and triturated. The precipitated crystals were filtered off to give 7.53 g of 4-chloro-6-dimethylamino-5-nitropyrimidine.

(ii) Preparation of 4-dimethylamino-6-ethoxy-5-nitropyrimidine:

To a mixture of 3.04 g of 4-chloro-6-dimethylamino5-nitropyrimidine obtained in (i) and 20 ml of ethanol was added dropwise a mixture of 60% oily sodium hydride (0.72 g) and 10 ml of ethanol with water cooling and stirring, and the resultant mixture was stirred at room temperature for 1 hour and refluxed with heating for 2.5 hours. The mixture was concentrated in vacuo to remove the solvent, and the residue was mixed with water. The precipitated crystals were filtered and washed with water to give 2.55 g of 4-dimethylamino-6-ethoxy-5-nitropyrimidine.

(iii) A mixture of 3 g of iron dust, 0.3 g of acetic acid and 2.5 ml of water was refluxed with heating for 30 minutes, allowed to cool at 80° C. and mixed with 10 ml of 2-propanol and gradually 2.33 g of 4-dimethylamino-6-ethoxy-5-nitropyrimidine. The resultant mixture was stirred at the same temperature for 1 hour, allowed to cool at 40° C., mixed with solution of 0.9 g of potassium carbonate in 1.5 ml of water and stirred for further 1 hour. Acetone was added to the mixture, which was filtered through Celite. The filtrate was concentrated in vacuo, and the residue was mixed with water and shaken with ether. The organic layer was washed with water and saturated saline in order, dried over anhydrous sodium sulfate and the solvent evaporated to give 1.80 g of the titled compound.

$^1$H-NMR(CDCl$_3$-TMS): δ = 1.42 (3H, t), 2.88 (6H, s), 3.47 (2H, br. s), 4.30 (2H, q), 8.05 (1H, s).

Example 30

Preparation of (R)-1-[2-(2, 3-methylenedioxyphenyl) heptyl]-3-(4-dimethylamino-6-ethoxypyrimidine-5-yl) urea (Compound No. 221 in Table 10)

A mixture of 0.66 g of 5-amino-4-dimethylamino-6-methoxypyrimidine, 1.28 g of N-ethoxycarbonyl-(R)-2-(2, 3-methylenedioxyphenyl) heptylamine, 0.55 g of 1, 8-diazabicyclo [5, 4, 0] undec-7-ene and 10 ml of dioxane was stirred at 100° C. for 16 hours and the solvent evaporated. The residue was chromatographed on a silica gel column, eluting with ethyl acetate-n-hexane (2:1–3:1), and the product was dissolved in ether. The solution was washed with water and saturated saline in this order, dried over anhydrous sodium sulfate and the solvent evaporated. The residue was triturated with n-hexane to give 0.63 g of the titled compound. mp. 62°–64° C.

$^1$H-NMR(CDCl$_3$-TMS): δ = 0.83 (3H, t), 1.22 (6H, m), 1.32 (3H, t), 1.62 (2H, m), 2.90 (1H, m), 2.96 (6H, s), 3.37 (1H, m), 3.55 (1H, m), 4.32 (2H, q), 4.76 (1H, t), 5.44 (1H, s), 5.80, 5.82 (each 1H, s), 6.57 (1H, dd), 6.70 (1H, dd), 6.74 (1H, dd), 8.16 (1H, s).

Reference Example 22

Preparation of 3-methyl-4-(1-methylethoxy)-1-phenyl-5-pyrazolecarboxylic acid (i) Preparation of 3-methyl-4-(1-methylethoxy)-1-phenyl-5-pyrazolecarboxylic acid methyl:

A mixture of 3.02 g of 4-hydroxy-3-methyl-1-phenyl-5-pyrazolecarboxylic acid methyl, 2.43 g of isopropyl iodide, 2.52 g of potassium carbonate and 20 ml of acetone was refluxed with heating and stirring for 19 hours. (Three hours later, 0.44 g of isopropyl iodide and 0.36 g of potassium carbonate were added additionally.) The reaction mixture was allowed to cool at room temperature and the salt was filtered off. The filtrate was concentrated in vacuo, and the residue was chromatographed on a silica gel column, eluting with ethyl acetate-n-hexane (1:7) to give 3.42 g of 3-methyl-4-(1-methylethoxy)-1-phenyl-5-pyrazolecarboxylic acid methyl.

$^1$H-NMR(CDCl$_3$-TMS): δ = 1.35 (6H, d), 2.28 (3H, s), 3.78 (3H, s), 4.34 (1H, obs. quint), 7.26–7.45 (5H, m).

The following compounds were prepared similarly.

1, 3-dimethyl-4-(1-methylethoxy)-5-pyrazolecarboxylic acid methyl:

δ = 1.29 (6H, d), 2.19 (3H, s), 3.90 (3H, s), 4.04 (3H, s), 4.19 (1H, obs. quint).

3-methyl-4-(1-methylethoxy)-1-(1-methylethyl)-5-pyrazolecarboxylic acid methyl:

δ = 1.28 (6H, d), 1.43 (6H, d), 2.20 (3H, s), 3.89 (3H, s), 4.15 (1H, obs. quint), 5.32 (1H, obs. quint).

(1, 1-dimethylethyl)-3-methyl-4-(1-methylethoxy)-5-pyrazolecarboxylic acid ethyl:

δ = 1.25 (6H, d), 1.40 (3H, t), 1.62 (9H, s), 2.17 (3H, s), 4.12 (1H, obs. quint), 4.35 (2H, q).

(ii) To a solution of 2.74 g of 3-methyl-4-(1-methylethoxy)1-phenyl-5-pyrazolecarboxylic acid methyl ester, obtained in (i), in 20 ml of methanol was added a solution of 0.80 g of sodium hydroxide in 5 ml of water, and the resultant mixture was refluxed with heating for 1.5 hours. The methanol was evaporated in vacuo, and the residue was dissolved in water to give a solution, which was mixed with conc. hydrochloric acid. The precipitated crystals were filtered and washed with water to give 2.53 g of 3-methyl-4-(1-methylethoxy )-1-phenyl-5-pyrazolecarboxylic acid.

$^1$H-NMR(CDCl$_3$-TMS): δ = 1.41 (6H, d ), 2.36 (3H, s ), 4.55 (1H, obs. quint), 7.39–7.45 (5H, m).

The following compounds were prepared similarly.

1, 3-dimethyl-4-(1-methylethoxy)-5-pyrazolecarboxylic acid:

$^1$H-NMR (CDCl$_3$-TMS): δ = 1.37 (6H, d), 2.27 (3H, s), 4.07 (3H, s ), 4.49 (1H, obs. quint).

3-methyl-4-(1-methylethoxy)-1-(1-methylethyl) -5-pyrazolecarboxylic acid:

$^1$H-NMR (CDCl$_3$-TMS): δ = 1.37 (6H, d), 1.44 (6H, d), 2.29 (3H, s), 4.50 (1H, obs. quint), 5.46 (1H, obs. quint).

1-(1, 1-dimethylethyl)-3-methyl-4-(1-methylethoxy)-5-pyrazolecarboxylic acid:

$^1$H-NMR (CDCl$_3$-TMS): δ = 1.38 (6H, d), 1.69 (9H, s), 2.27 (3H,s), 4.50 (1H, obs. quint).

Example 31

Preparation of (R)-1-[2-(2, 3-methylenedioxyphenyl) heptyl]-3-[3-methyl-4-(1-methylethoxy)-1-phenyl-pyrazole-5-yl]urea (Compound No. 248 in Table 12)

A mixture of 0.91 g of 3-methyl-4-(1-methylethoxy)-1-phenyl-5-pyrazolecarboxylic aid, 0.96 g of diphenylphosphoryl azide, 0.43 g of triethylamine and 15 ml of toluene was stirred at 80° C. for 3 hours and allowed to cool with ice. To the mixture was added a solution of 0.82 g of (R)-2-(2, 3-methylenedioxyphenyl)heptylamine in 8 ml of toluene with ice cooling and stirring, and the resultant mixture was stirred at room temperature for 3 hours and concentrated in vacuo. The residue was chromatographed on a silica gel column, eluting with ethyl acetate-n-hexane (1:3→1:2) to give 1.42 g of the titled compound.

mp. 125.5°–126.5° C.

¹H-NMR (CDCl₃-TMS): δ=0.83 (3H, t), 1.20 (6H, d), 1.21 (6H, m), 1.62 (2H, m), 2.23 (3H, s), 2.86 (1H, obs. quint), 3.36 (1H, m), 3.54 (1H, m), 4.12 (1H, obs. quint), 5.34 (1H, t), 5.70 (1H, s), 5.76, 5.80 (each 1H, s), 6.57 (1H, dd), 6.66 (1H, dd), 6.72 (1H, dd), 7.31–7.43 (5H, m).

Example 32

Preparation of (R)-1-[2-(2, 3-methylenedioxyphenyl) heptyl ]-3-[1, 3-dimethyl-4-(1-methylethoxy)pyrazole-5-yl]-urea (Compound No. 249 in Table 12)

Using 1, 3-dimethyl-4-(1-methylethoxy)-5-pyrazolecarboxylic acid in place of 3-methyl-4-(1-methylethoxy)-1-phenyl-5-pyrazolecarboxylic acid in Example 31, the reaction was effected in the same manner as in Example 31 to give the titled compound.

mp. 123°–124° C.

¹H-NMR (CDCl₃-TMS): δ=0.81 (3H, t), 1.16 (6H, d), 1.22 (6H, m), 1.63 (2H, m), 2.14 (3H, s), 2.88 (1H, obs. quint), 3.35 (1H, m), 3.49 (3H, s), 3.55 (1H, m), 4.00 (1H, obs. quint), 4.88 (1H, t), 5.82, 5.84 (each 1H, s), 5.94 (1H, s), 6.59 (1H, dd), 6.66 (1H, dd), 6.73 (1H, dd).

Example 33

Preparation of (R)-1-[2-(2, 3-methylenedioxyphenyl) heptyl]-3-[3-methyl-4-(1-methylethoxy)-1-(1-methlethyl) pyrazole-5-yl]urea (Compound No. 250 in Table 12)

Using 3-methyl-4-(1-methylethoxy)-1-(1-methylethyl)-5-pyrazolecarboxylic acid in place of 3-methyl-4-(1-methylethoxy)-1-phenyl-5-pyrazolecarboxylic acid in Example 31, the reaction was effected in the same manner as in Example 31 to give the titled compound as amorphous solid.

¹H-NMR (CDCl₃-TMS): δ=0.83 (3H, t), 1.16 (6H, d), 1.22 (6H, m), 1.31 (6H, dd), 1.61 (2H, m), 2.16 (3H, s), 2.87 (1H, obs. quint), 3.35 (1H, m), 3.54 (1H, m), 3.99 (1H, obs. quint), 4.31 (1H, obs. quint), 4.91 (1H, t), 5.80 (2H, s), 5.82 (1H, s), 6.57 (1H, dd), 6.66 (1H, dd), 6.72 (1H,dd).

Example 34

Preparation of (R)-1-[2-(2, 3-methylenedioxyphenyl) heptyl]-3-[1-(1, 1-dimethylethyl)-3-methyl-4-(1-methylethoxy) pyrazole-5-yl]urea (Compound No. 251 in Table 12)

Using 1-(1, 1-dimethylethyl)-3-methyl-4-(1-methylethoxy)-5-pyrazolecarboxylic acid in place of 3-methyl-4-(1-methylethoxy)-1-phenyl-5-pyrazolecarboxylic acid in Example 31, the reaction was effected in the same manner as in Example 31 to give the titled compound.

mp. 98.5°–99° C.

¹H-NMR(CDCl₃-TMS): δ=0.83 (3H,t), 1.17 (6H,d), 1.22 (6H,m), 1.47 (9H,s), 1.62 (2H,m), 2.14 (3H,s), 2.86 (1H, obs. quint), 3.37 (1H,m), 3.51 (1H,m), 4.03 (1H, obs. quint), 4.86 (1H, t), 5.50 (1H, s), 5.80 (2H, s), 6.57 (1H, dd), 6.66 (1H, dd), 6.71 (1H, dd).

Example 35

Preparation of (R)-1-[2-(2, 3-methylenedioxyphenyl) heptyl]-3-(4-ethoxycarbonyl-1-phenylpyrazole-5-yl) urea (Compound No. 252 in Table 12)

To a mixture of 1.16 g of 5-amino-1-phenylpyrazole-4-carboxylic acid ethyl ester and 10 ml of methylene chloride were dropwise added 0.53 g of bis (trichloromethyl) carbonate and 1.11 g of triethylamine in order with ice cooling and stirring, and the resultant mixture was refluxed with heating for 4 hours. The reaction mixture was allowed to cool to room temperature, mixed with a solution of 1.18 g of (r)-2-(2, 3-methylenedioxyphenyl) heptylamine in 3 ml of methylene chloride, stirred at room temperature for 2 hours and the solvent evaporated. Water was added to the residue, and the mixture was extracted with ethyl acetate. The organic layer was washed with saturated saline, dried over anhydrous sodium sulfate and the solvent evaporated. The residue was chromatographed on a column of silica gel, eluting with ethyl acetate and n-hexane (2:5) to give 1.94 g of the titled compound as amorphous solid.

¹H-NMR (CDCl₃-TMS): δ=0.82 (3H, t), 1.20 (6H, m), 1.35 (3H, t), 1.54 (2H, m), 2.78 (1H, m), 3.18 (1H, m), 3.45 (1H, m), 4.29 (2H, q), 4.83 (1H, t), 5.88, 5.90 (each 1H, s), 6.57 (1H, dd), 6.71–6.82 (2H, m), 7.32–7.52 (5H+1H, m), 7.94 (1H, s).

Example 36

Preparation of (R)-1-[2-(2, 3-methylenedioxyphenyl) heptyl]-3-(3, 5-di-2-pyridyl-4H-1, 2, 4-triazole-4-yl)urea (Compound No. 288 in Table 13)

To a mixture of 1.19 g of 4-amino-3, 5-di-2-pyridyl-4H-1 2, 4-triazole and 10 ml of methylene chloride were dropwise added 0.53 g of bis(trichloromethyl) carbonate and 1.11 g of triethylamine with ice cooling and stirring, and the resultant mixture was refluxed with heating for 17 hours. 0.53 g of bis(trichloromethyl) carbonate and 1.11 G of triethylamine were added 14 hours later. The reaction mixture was allowed to cool to room temperature, mixed with a solution of 1.18 g of (R)-2-(2, 3-methylenedioxyphenyl) heptylamine in 3 ml of methylene chloride and stirred at room temperature for 6 hours. The reaction mixture was washed with saturated saline, dried over anhydrous sodium sulfate and the solvent evaporated. The residue was chromatographed on a silica gel column, eluting with ethyl acetate-acetone (7/1→5/1) to give 1.66 g of the titled compound.

mp. 162°–163° C.

¹H-NMR (CDCl₃-TMS): δ=0.79 (3H, t), 1.12 (6H, m), 1.49 (2H, m), 2.79 (1H, obs. quint), 3.33 (1H, m), 3.45 (1H, m), 5.80, 5.82 (each 1H, s), 5.85 (1H, br. s), 6.48 (1H, dd), 6.61–6.68 (2H, m), 7.37 (2H, dd), 7.86 (2H, dt), 8.22 (2H, d), 8.53 (2H, d), 9.33 (1H, s).

The compounds as shown in Tables 1–13 above can be prepared in the same manner as in Examples 1–30.

EXPERIMENT

ACAT inhibition of the compounds of the present invention were assayed by the following method. HepG2 cell coming from human hepatic cancer cell was used for assaying ACAT activity. Thus, the assay was effected by adding radioactivity labelled oleic acid-bovine serum albumin complex into an incubation solution of HepG2 cell and measuring the amount of radioactivity labelled cholesterol oleate produced from the radioactivity labelled oeleic acid within the cell. Therefore, the activity of the compound of this invention to inhibit ACAT was obtained by calculating how much percent lowered the productivity of cholesterol oleate in control group containing no test compound by adding the test compound in each concentration (μM) and then expressing IC$_{50}$ value, namely concentration of a test compound required to inhibit 50% expression of enzyme. Table 14 shows the result.

TABLE 14

| Example No | IC$_{50}$ (μM) |
|---|---|
| 1 | 0.01 |
| 2 | 0.003 |
| 3 | 0.018 |
| 4 | 0.0065 |
| 8 | 0.01 |
| 9 | 0.05 |
| 10 | 0.0076 |
| 17 | 0.0009 |
| 18 | 0.101 |
| 20 | 0.037 |
| 21 | 0.154 |
| 22 | 0.139 |
| 23 | 0.195 |
| 24 | 0.230 |
| 25 | 0.057 |
| 26 | 0.175 |
| 29 | 0.314 |
| 30 | 0.109 |
| 31 | 0.028 |
| 34 | 0.106 |

EFFECT OF THE INVENTION

The compounds of the present invention are expected to be useful as medicinals for treating hyperlipemia and atherosclerosis, showing potent ACAT inhibitory activity.

What is claimed:

1. A carboxamide derivative of the formula:

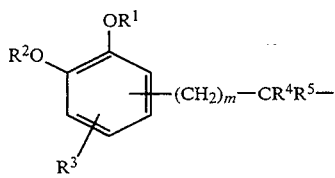

wherein, m, n and q each independently represent an integer from 0 to 3, p represents 0 or 1, $R^1$ and $R^2$ each independently represent C$_1$–C$_3$ alkyl group, or $R^1$ and $R^2$, taken together, may form C$_1$–C$_3$ alkylene group, $R^3$ represents hydrogen atom, amino group, C$_1$–C$_3$ alkylamino group, C$_2$–C$_6$ dialkylamino group, C$_1$–C$_3$ alkyl group, C$_2$–C$_7$ acyl group, pyrrolidino group, piperidino group, morpholino group, nitro group, hydroxy group, C$_2$–C$_7$ acyloxy group, C$_1$–C$_3$ alkoxy group or halogen atom, $R^4$ represents hydrogen atom or C$_1$–C$_{10}$ alkyl group, $R^5$ represents C$_1$–C$_{10}$ alkyl group, or $R^4$ and $R^5$, taken together, may form C$_2$–C$_7$ alkylene group, A ring represents;

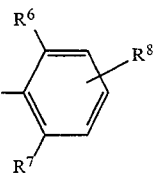

wherein $R^6$ and $R^7$ each independently represent C$_1$–C$_5$ alkyl group, C$_1$–C$_5$ alkoxy group, or halogen atom, $R^8$ represents hydrogen atom, amino group, C$_1$–C$_3$ alkylamino group, C$_2$–C$_6$ dialkylamino group, C$_1$–C$_5$ alkyl group, C$_1$–C$_5$ alkoxy group, pyrrolidino group, piperidino group, morpholino group or halogen atom, or A ring represents;

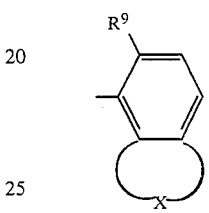

wherein $R^9$ represents hydrogen atom, C$_1$–C$_5$ alkyl group or C$_1$–C$_5$ alkoxy group and X represents;

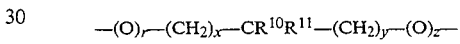

in which $R^{10}$ and $R^{11}$ each independently represent hydrogen atom or C$_1$–C$_5$ alkyl group, r and z each independently represent 0 or 1, and x and y each independently represent an integer from 0 to 5 under the condition that $0 \leq x+y \leq 5$; or A ring represents;

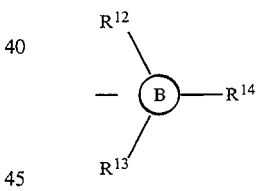

wherein B ring represents 5 or 6-membered nitrogen-containing aromatic group, $R^{12}$ and $R^{13}$ each independently represent C$_1$–C$_5$ alkyl group, optionally substituted phenyl group or piperazino group, pyridyl group, C$_1$–C$_5$ alkoxy group, a group

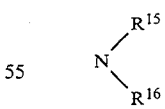

(in which $R^{15}$ and $R^{16}$ each independently represent hydrogen atom or C$_1$–C$_5$ alkyl group, or $R^{15}$ and $R^{16}$, taken together, may form C$_3$–C$_6$ alkylene group), morpholino group, carboxy group or C$_2$–C$_4$ alkoxycarbonyl group, $R^{14}$ represents hydrogen atom or C$_1$–C$_5$ alkyl group, with the proviso that $R^{12}$ and $R^{13}$ are attached to the two atoms adjacent to the atom on the B ring which is bound to the moiety:

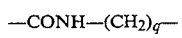

(in which q has the same significance as defined above), with the proviso that when A ring is

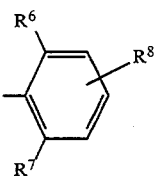

in which $R^6$, $R^7$ and $R^8$ have the same significance as defined above, then p represents 0) a pharmaceutically acceptable salt thereof.

2. A compound according to claim 1, in which $R^3$ represents hydrogen atom, amino group, $C_1$-$C_3$ alkylamino group, $C_2$-$C_6$ dialkylamino group, $C_1$-$C_3$ alkyl group, $C_2$-$C_7$ acyl group, hydroxy group, $C_2$-$C_4$ acyloxy group, $C_1$-$C_3$ alkoxy group or halogen group, $R^4$ represents hydrogen atom, $R^5$ represents $C_1$-$C_{10}$ alkyl group, or $R^4$ and $R^5$ taken together, may form $C_2$-$C_7$ alkylene group, and A ring represents;

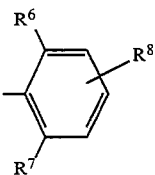

wherein $R^6$ and $R^7$ have the same significance as defined in claim 1 above, and $R^8$ represents hydrogen atom, amino group, $C_1$-$C_3$ alkylamino group, $C_2$-$C_6$ dialkylamino group, $C_1$-$C_5$ alkyl group, $C_1$-$C_3$ alkoxy group or halogen atom, or;

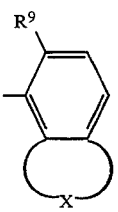

wherein $R^9$ and X have the same significance as defined in claim 1 above, or;

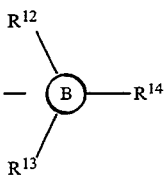

wherein B ring and $R^{14}$ have the same significance as defined in claim 1 above, and $R^{12}$ and $R^{13}$ each independently represent $C_1$-$C_5$ alkyl group, phenyl group, pyridyl group, $C_1$-$C_5$ alkoxy group, a group:

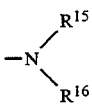

in which $R^{15}$ and $R^{16}$ have the same significance as defined in claim 1 above, morpholino group or $C_2$-$C_4$ alkoxycarbonyl group.

3. A compound according to claim 1, in which m, p and q each independently represent 0 or 1, n represents 0, 1 or 2, $R^3$ represents hydrogen atom, $C_2$-$C_6$ dialkylamino group or $C_2$-$C_4$ acyl group, $R^4$ represents hydrogen atom, $R^5$ represents $C_1$-$C_8$ alkyl group, and A ring represents;

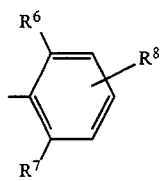

wherein $R^6$ and $R^7$ each independently represent $C_1$-$C_5$ alkyl group, $C_1$-$C_3$ alkoxy group or halogen atom, $R^8$ represents hydrogen atom, $C_2$-$C_8$ dialkylamino group, $C_1$-$C_3$ alkoxy group or halogen atom, or A ring represents;

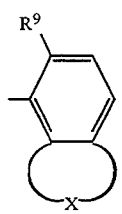

wherein $R^9$ represents hydrogen atom or $C_1$-$C_3$ alkoxy group, and X represents;

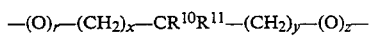

in which $R^{10}$ and $R^{11}$ each independently represent hydrogen atom or $C_1$-$C_3$ alkyl group, r and z have the same significance as defined in claim 1, and x and y are each independently an integer from 0 to 3 under condition that $0 \leq x+y \leq 3$, or A ring represents;

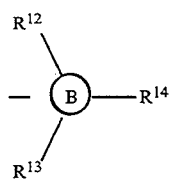

wherein B ring represents pyrimidine ring, pyrazole ring or triazole ring, $R^{12}$ and $R^{13}$ each independently represent $C_1$-$C_5$ alkyl group, phenyl group, pyridyl group or $C_1$-$C_5$ alkoxy group, or a group:

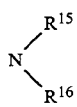

(in which $R^{15}$ and $R^{16}$ each independently represent $C_1$-$C_3$ alkyl group, or $R^{15}$ and $R^{16}$, taken together, may form $C_3$-$C_5$ alkylene group, morpholino group or $C_2$-$C_4$ alkoxycarbonyl group) and $R^{14}$ represents hydrogen atom or $C_1$-$C_3$ alkyl group.

4. A compound according to claim 1, in which m and q represent 0, n represents 0, 1 or 2, p represents 0 or 1, $R^3$ represents hydrogen atom, $C_2$-$C_6$ dialkylamino group or $C_2$—$C_4$ acyl group, $R^4$ represents hydrogen atom, $R^5$ represents $C_1$-$C_8$alkyl group, A ring represents;

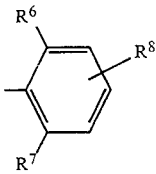

wherein $R^6$ and $R^7$ each independently represent $C_1$-$C_5$ alkyl group and $R^8$ represents hydrogen atom or $C_2$-$C_6$ dialkylamino group, or A ring represents;

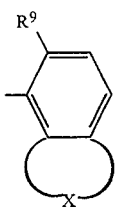

wherein $R^9$ represents hydrogen atom or $C_1$-$C_5$ alkoxy group, and X represents;

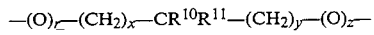

—(O)$_r$—(CH$_2$)$_x$—CR$^{10}$R$^{11}$—(CH$_2$)$_y$—(O)$_z$— in which $R^{10}$ and $R^{11}$ each independently represent hydrogen atom or $C_1$-$C_3$ alkyl group, r and z have the same significance as defined in claim 1 above, x and y each independently represent an integer from 0 to 3 under condition that $0 \leq x+y \leq 3$, or A ring represents;

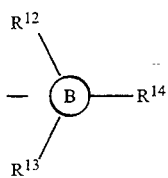

in which B ring represents pyrimidine ring or pyrazole ring, $R^{12}$ and $R^{13}$ each independently represent $C_1$-$C_5$ alkyl group, phenyl group, $C_1$-$C_5$ alkoxy group, a group:

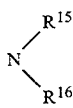

(in which $R^{15}$ and $R^{16}$ each independently represent $C_1$-$C_3$ alkyl group, or $R^{15}$ and $R^{16}$ taken together, may form $C_3$-$C_5$ alkylene group, or morpholino group), and $R^{14}$ represents hydrogen atom or $C_1$-$C_3$ alkyl group.

5. A compound according to claim 1, in which m and q represent 0, n represents 1, p represents 0 or 1, $R^1$ and $R^2$ taken together form $C_1$-$C_3$ alkylene group, $R^3$ and $R^4$ represent hydrogen atom, $R^5$ represents $C_4$-$C_7$ alkyl group, A ring represents;

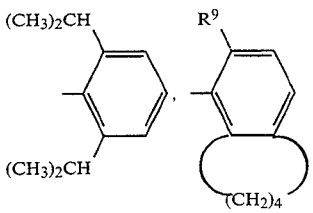

wherein $R^9$ represents $C_1$-$C_5$ alkoxy group, or;

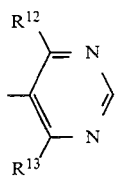

in which $R^{12}$ and $R^{13}$ each independently represent $C_1$-$C_3$ alkoxy group, or;

in which $R^{15}$ and $R^{16}$ represent $C_1$-$C_3$ alkyl group, or $R^{15}$ and $R^{16}$, taken together, form $C_3$-$C_5$ alkylene group.

6. A compound according to claim 1, in which m and q represent 0, n represents 1, p represents 0 or 1, $R^1$ and $R^2$ taken together form methylene group, $R^3$ and $R^4$ represent hydrogen atom, $R^5$ represents pentyl group, and A ring represents;

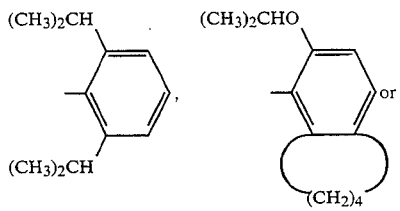

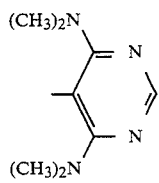

7. A pharmaceutical composition comprising a pharmaceutically effective amount of a compound according to claim 1 and at least one pharmaceutically acceptable carrier therefor.

* * * * *